United States Patent
Nagarkar

(10) Patent No.: US 7,692,156 B1
(45) Date of Patent: Apr. 6, 2010

(54) BEAM-ORIENTED PIXELLATED SCINTILLATORS FOR RADIATION IMAGING

(75) Inventor: Vivek Nagarkar, Weston, MA (US)

(73) Assignee: Radiation Monitoring Devices, Inc., Watertown, MA (US)

( * ) Notice: Subject to any disclaimer, the term of this patent is extended or adjusted under 35 U.S.C. 154(b) by 75 days.

(21) Appl. No.: 11/843,881

(22) Filed: Aug. 23, 2007

Related U.S. Application Data

(60) Provisional application No. 60/839,888, filed on Aug. 23, 2006.

(51) Int. Cl.
*G01T 1/20* (2006.01)
(52) U.S. Cl. .............. 250/370.11; 250/370.09; 250/361 R
(58) Field of Classification Search .................. None
See application file for complete search history.

(56) References Cited

U.S. PATENT DOCUMENTS

| | | | |
|---|---|---|---|
| 4,041,315 A * | 8/1977 | Hounsfield | 378/11 |
| 4,845,363 A * | 7/1989 | Akai | 250/368 |
| 5,171,996 A | 12/1992 | Perez-Mendez | |
| 5,227,633 A * | 7/1993 | Ryuo et al. | 250/367 |
| 5,510,622 A | 4/1996 | Hu et al. | |
| 5,519,227 A * | 5/1996 | Karellas | 250/483.1 |
| 5,757,951 A | 5/1998 | Tuy | |
| 5,773,829 A * | 6/1998 | Iwanczyk et al. | 250/367 |
| 6,087,618 A | 7/2000 | Wiener-Avnear et al. | |
| 6,518,778 B2 * | 2/2003 | Vig et al. | 324/727 |
| 6,798,717 B2 | 9/2004 | Wiener-Avnear et al. | |
| 6,823,038 B2 * | 11/2004 | Von Der Haar | 378/19 |
| 6,944,263 B2 | 9/2005 | Xiao et al. | |
| 7,217,928 B2 | 5/2007 | Crosetto | |
| 2001/0013510 A1 | 8/2001 | Wiener-Avnear et al. | |
| 2002/0067796 A1 | 6/2002 | Hoffman | |
| 2002/0070343 A1 * | 6/2002 | Hoffman | 250/367 |
| 2003/0021374 A1 * | 1/2003 | Venkataramani et al. | 378/19 |
| 2004/0109532 A1 * | 6/2004 | Ford et al. | 378/57 |
| 2004/0114467 A1 | 6/2004 | Wiener-Avnear et al. | |
| 2004/0239941 A1 * | 12/2004 | Schramm et al. | 356/479 |
| 2004/0251420 A1 * | 12/2004 | Sun | 250/370.09 |
| 2005/0092943 A1 * | 5/2005 | Nitsche et al. | 250/586 |
| 2005/0265517 A1 * | 12/2005 | Gary | 378/21 |
| 2006/0000978 A1 * | 1/2006 | Engdahl et al. | 250/363.1 |

(Continued)

OTHER PUBLICATIONS

Birnie, Dunbar, "Coating Quality and Spin Coating", published Jan. 11, 2001. Retrieved from the Internet [Nov. 25, 2008]; Retrieved from URL: <http://www.mse.arizona.edu/faculty/birnie/Coatings/>.*

(Continued)

*Primary Examiner*—David P Porta
*Assistant Examiner*—Yara B Green
(74) *Attorney, Agent, or Firm*—Townsend and Townsend and Crew LLP

(57) ABSTRACT

The present invention provides radiation detectors and methods, including radiation detection devices having beam-oriented scintillators capable of high-performance, high resolution imaging, methods of fabricating scintillators, and methods of radiation detection. A radiation detection device includes a beam-oriented pixellated scintillator disposed on a substrate, the scintillator having a first pixel having a first pixel axis and a second pixel having a second pixel axis, wherein the first and second axes are at an angle relative to each other, and wherein each axis is substantially parallel to a predetermined beam direction for illuminating the corresponding pixel.

63 Claims, 12 Drawing Sheets

U.S. PATENT DOCUMENTS

| | | | |
|---|---|---|---|
| 2006/0145081 A1 | 7/2006 | Hawman | |
| 2006/0159221 A1 | 7/2006 | Popescu | |
| 2006/0237654 A1* | 10/2006 | Srivastava et al. | 250/370.11 |
| 2007/0086565 A1* | 4/2007 | Thompson et al. | 378/19 |
| 2007/0127122 A1* | 6/2007 | Bolt et al. | 359/509 |
| 2009/0134334 A1* | 5/2009 | Nelson | 250/361 R |

OTHER PUBLICATIONS

Akarapu et al., "A Thermal Stress and Failure Model for Laser Cutting and Forming Operations," *J. Failure Analysis and Prevention* 4:51-62 (2004).

Akarapu and Li, "A 3-D Numerical Model for Ablation Phenomena and Thermal Stress Evolution During Laser Machining," *Proceedings of HT2003, ASME Summer Heat Transfer Conference*, pp. 189-198 (2003).

Akarapu and Segall, "Finite Element Modeling of Ablation Phenomena and Thermal Stress Evolution During a Unique Application of Dual Laser Cutting of Ceramics," *Energy Efficient Manufacturing Processes, The MPMD Fourth Global Innovations Symposium of The Minerals, Metals & Materials Society*, pp. 87-98 (2003).

Akarapu and Segall, "Investigation of an Active Stressing Technique For Delaying Fracture During Laser Cutting of Alumina," *Proceedings of IMECE04, ASME International Mechanical Engineering Congress and Exposition*, pp. 173-179 (2004).

Pereles-Santiago et al., "Faster and damage-reduced laser cutting of thick ceramics using a simultaneous prescore approach," *J. Laser Applications* 17:219-224 (2005).

Segall et al., "Fracture control of unsupported ceramics during laser machining using a simultaneous prescore," *J. Laser Applications* 17:57-62 (2005).

\* cited by examiner

FIG. 5
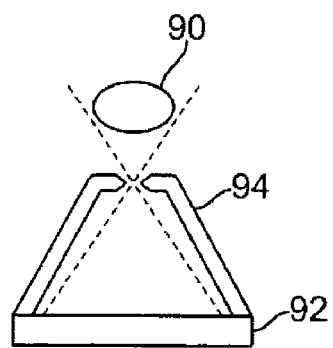
FIG. 5A
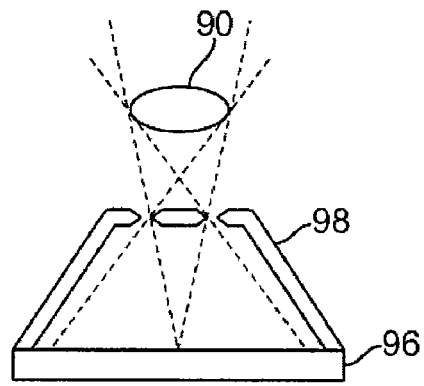
FIG. 5B
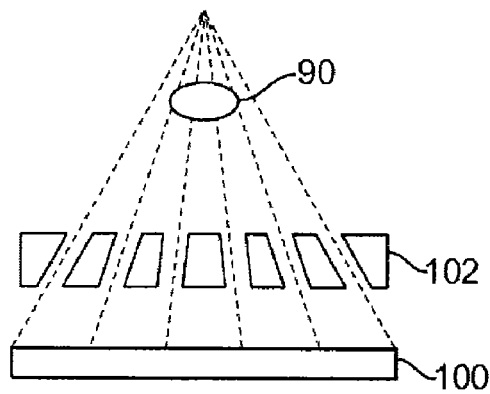
FIG. 5C
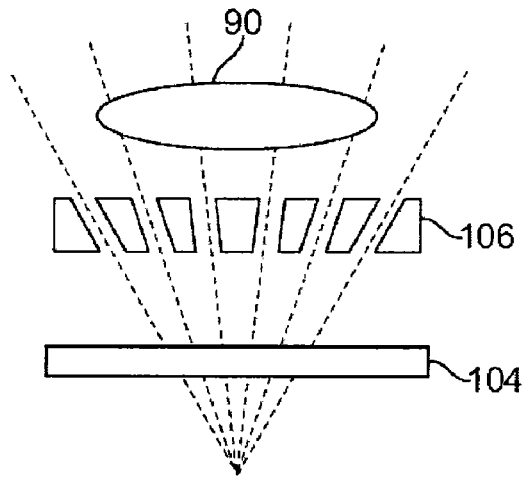
FIG. 5D

FIG. 6
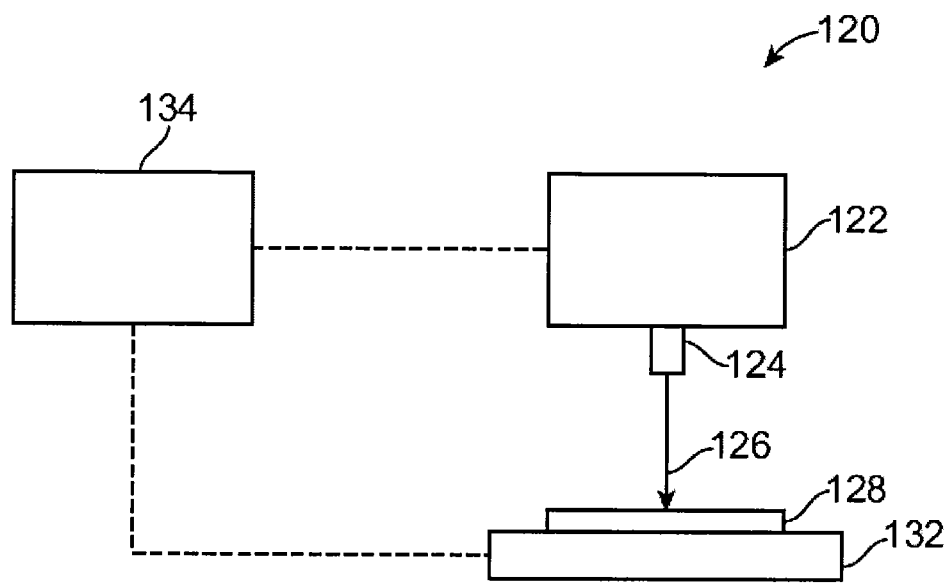
FIG. 6A
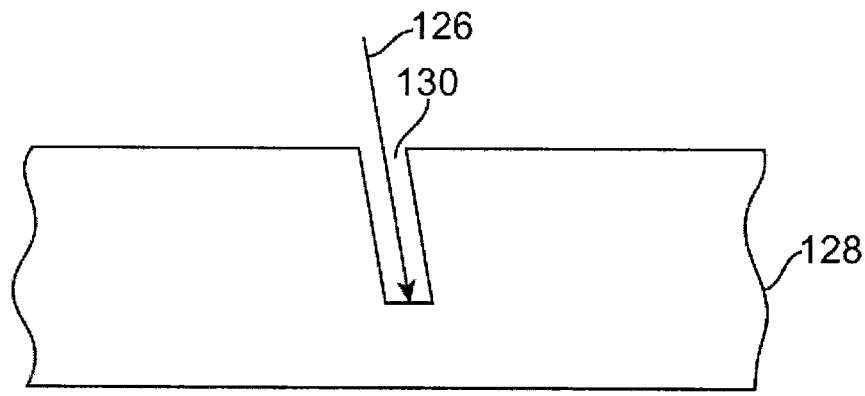
FIG. 6B

A

B

A

B

A

B

A

B

A

B

C

D

BEAM-ORIENTED PIXELLATED SCINTILLATORS FOR RADIATION IMAGING

CROSS-REFERENCES TO RELATED APPLICATIONS

This application claims the benefit under 35 U.S.C. §119 (e) of U.S. Patent Application No. 60/839,888, filed Aug. 23, 2006, the entire content of which is incorporated herein by reference.

BACKGROUND OF THE INVENTION

The present invention relates generally to radiation detectors and methods. More specifically, the present invention relates to radiation detection devices and methods, including radiation detectors having beam-oriented pixellated scintillators capable of high-performance, high resolution imaging.

Scintillation spectrometers are widely used in detection and spectroscopy of energetic photons and/or particles (e.g., X-rays and gamma-rays). Such detectors are commonly used, for example, in nuclear and particle physics research, medical imaging, diffraction, non destructive testing, nuclear treaty verification and safeguards, nuclear non-proliferation monitoring, and geological exploration.

A wide variety of scintillators are now available and new scintillator compositions are being developed. Among currently available scintillators, thallium-doped alkali halide scintillators have proven useful and practical in a variety of applications. One example includes thallium doped cesium iodide (CsI(Tl)), which is a highly desired material for a wide variety of medical and industrial applications due to its excellent detection properties, low cost, and easy availability. Having a high conversion efficiency, a rapid initial decay, an emission in the visible range, and cubic structure that allows fabrication into micro-columnar films (see, e.g., U.S. Pat. No. 5,171,996), CsI(Tl) has found use in radiological imaging applications. Furthermore, its high density, high atomic number, and transparency to its own light make CsI(Tl) a material of choice for medical imaging applications, such as X-ray and gamma-ray spectroscopy, Single Photon Emission Computed Tomography or SPECT, positron emission tomography (PET), and the like.

Scintillation spectrometry generally comprises a multi-step scheme. Specifically, scintillators work by converting energetic particles such as X-rays, gamma-rays, and the like, into a more easily detectable signal (e.g., visible light). Incident energetic photons are stopped by the scintillator material of the device and, as a result, the scintillator produces light photons mostly in the visible light range that can be detected, e.g., by a suitably placed photodetector. The detected light photons from the scintillator can then be processed and converted into other signals and thus can be used in generating an image, such as an image of a patient or a portion of the patient's body (e.g., internal organs, etc.).

Many nuclear medicine imaging techniques, such as SPECT and PET, require high spatial resolution in order to generate a desired image due, for example, to factors such as the small scale of the details being imaged, as well as the complexity of the detection and estimation tasks. Unfortunately, existing medical imaging instrumentation, such as SPECT instrumentation, is often restrictively expensive and often does not provide the required performance needed for certain applications, such as study and analysis of biological processes and activity of pharmaceutical agents in vivo. As such, the development of a high-resolution detector combined with energy discrimination capabilities is essential for the improvement of future imaging devices For example, one important factor limiting high-resolution radiation imaging in existing systems is the high potential for parallax errors that degrade and/or limit image quality. Parallax errors or depth of interaction (DOI) errors occur when an energetic photon strikes the detector surface at a given angle of incidence (angle $\theta$). Where the scintillator material has a linear attenuation coefficient $\mu$, and the mean depth of interaction is given by $\mu^{-1}$ and the linear displacement due to parallax error in a direction parallel to the surface of the scintillator can be calculated as $\mu^{-1} \sin \theta$. Parallax errors for imaging lower energy radiation sources are less significant and generally smaller than the spatial resolution limit imposed by realistic values of a collimator pinhole diameter (e.g., >100 µm). However, for imaging higher energy photons (e.g., gamma-rays), these errors are significantly large, resulting in a significant degradation of spatial resolution.

Parallax error can be a fundamental problem in many radiation imaging systems having conventional scintillators or even with existing high-resolution, microcolumnar CsI(Tl) scintillators, particularly where a high spatial resolution is desired. For example, the parallax errors arising from the depth of penetration of the incident energetic photons (e.g., gamma-rays), such as in radionuclide imaging using a pinhole collimator and existing scintillators, can result in an undesirable line pattern in a generated image rather than a well defined point-like emission of light, substantially degrading performance of the detectors, including spatial resolution.

Thus, there is a need for improved scintillators and radiation detection and imaging devices, as well as related methods, including scintillators and radiation detectors capable of high-resolution, high performance imaging.

BRIEF SUMMARY OF THE INVENTION

The present invention provides beam-oriented pixellated scintillators and radiation detectors having significantly enhanced performance characteristics, including improved spatial resolution, due in part to reduction and/or minimization of parallax errors. Furthermore, the beam-oriented pixellated scintillators of the present invention can be coupled with readout sensors having high intrinsic spatial resolution, thereby further improving detector performance.

A beam-oriented pixellated scintillator of the present invention can include a scintillator or slab of scintillator material that is micro-pixellated to form an array of pixels separated by inter-pixel grooves. Pixels are oriented to form a beam-oriented array that is matched to the illumination directions of radiation beams reaching the pixels. The illumination directions of the radiation beams reaching the pixels may be selected or predetermined, for example, by controlling a radiation source or by use of a collimator, such as a pinhole or multi-pinhole collimator. The beam-oriented orientation of the pixels of the array ensures minimal parallax errors in localizing high-energy photon events (e.g., gamma-rays, etc.), thereby significantly improving detector performance.

Thus, in one aspect of the present invention, a radiation detection device comprising a beam-oriented pixellated scintillator is provided. The beam-oriented pixellated scintillator includes a first pixel having a first pixel axis and a second pixel having a second pixel axis, wherein the first and second pixel axes are at an angle relative to each other. For example, the scintillator can include an array of pixels, with the first and second pixels included in the array. Each axis is oriented so as to be substantially parallel to the predetermined beam direction at that pixel.

In another aspect, the present invention provides a radiation detection device comprising a beam-oriented pixellated scintillator having an array of pixels, with each pixel of the array having a pixel axis having an orientation selected to substantially match a predetermined illumination direction of a radiation beam reaching the pixel. At least one of the pixels of the array has an axis that is at an angle relative to another pixel axis of the array.

In another aspect, the present invention provides a radiation detection device for detecting radiation beams produced by a radiation source and illuminating the detection device at a plurality of different locations. The device includes a pixellated scintillator having a plurality of pixels, wherein each pixel comprises a pixel axis that is oriented substantially along a predetermined illumination direction of a radiation beam reaching the corresponding pixel. At least one of the pixels has a pixel axis that is oriented at an angle relative to a pixel axis of another pixel of the plurality.

Pixels of the present invention can include a variety of shapes and patterns, as well as spacings and/or arrangements on the scintillator. For example, pixels of the scintillator can include square, rectangular, rhomboidal, triangular, hexagonal shapes and the like. The pixels are separated by inter-pixel grooves, which can be formed, for example, by laser micromachining techniques. Inter-pixel grooves are not limited to any particular shape or dimension, and can include, for example, wedge or V-shaped grooves, parallel-sided grooves, rounded grooves, and the like. Grooves can extend through the entire thickness of the scintillator or partially through the scintillator. In one embodiment, for example, grooves can extend no farther through the slab of scintillator material than 200 µm from the uncut surface of the slab or the surface of the scintillator opposite the surface into which the groove is cut. In one particular embodiment, the pixels can form a continuous or monolithic array, rather than a collection of pixel elements that need to be individually assembled so as to form a robust array. The spacing between pixel centers will typically include about 100 µm to about 1 mm, and a monolithic array of pixels will contain at least 3×3 pixels.

A variety of different scintillator materials can be used in forming a beam-oriented pixellated scintillator of the present invention. Scintillators can include, for example, halides of various metals such as NaI(Tl), CsI(Tl), CsI(Na), CaF2(Eu), SrF2, BaF2, LiF(Eu), RbF2, CsF, NaF, brittle and thermally fragile oxides like LSO, GSO, BGO, CdWO4, ZnWO4, ceramic scintillators such as Lu2O3(Eu), GOS ceramic, and other important materials such as ZnSe(Te) In one particular embodiment, CsI(Tl) is used. In another embodiment, LaBr(Ce) and other lanthanide halide compositions are used. The scintillator material can include a crystal composition or compositions such as films, ceramics, and the like. The thickness of the scintillator material of the slab or beam-oriented scintillator will typically include a thickness of about 250 µm to about 1.5 cm.

The radiation detector of the present invention can additionally have one or more coatings or layers of material formed on a surface of the scintillator or on at least a portion of a pixel. Additional layers can include a protective layer, polymer protective layer, moisture protective layer, and/or an optically absorptive or reflective layer, and the like. In another embodiment, the scintillator further includes a heavy element slurry deposited in inter-pixel grooves of the scintillator to reduce inter-pixel radiation scatter. To enhance the light channeling, a suitable material having a refractive index lower than that of the scintillator material (e.g., CsI(Tl)) can be deposited and can surround individual pixel elements. For example, in one particular embodiment, to further enhance the light collection, a thin layer of reflective coating can be formed on top of the scintillator. A heavy element (lead, tungsten, bismuth) slurry can be introduced in the spaces or grooves around the individual pixels, reducing the transfer of energy from pixel to pixel by characteristic radiation and by Compton scattered photons.

In one embodiment, a beam-oriented pixellated scintillator can be coupled with or disposed on a substrate, for example, prior to or subsequent to pixel fabrication. A variety of substrates will be suitable for use in devices and methods of the present invention and can include, for example, various conformations (e.g., substantially flat, planar, non-planer, etc.) and compositions. Non-limiting examples of suitable substrates include optically reflective, non-reflective, transparent substrates, including, e.g., carbon, beryllium, boron, carbide, aluminum substrates and the like. In some embodiments, a beam-oriented scintillator of the invention can coupled directly to a photodetector, in which case the photodetector acts as a substrate. Various arrangements and/or configurations of a substrate and coupled beam-oriented scintillator are available and can include, for example, arrangements where the side of the substrate opposite the scintillator faces a direction from which a radiation beam is directed (e.g., radiation source), as well as where a side of the substrate opposite the scintillator faces a photodetector and the pixels of the beam-oriented scintillator face a direction from which the radiation beam is directed.

Thus, a radiation detection device of the present invention can additionally include a photodetector optically coupled to the scintillator. Various photodetectors and/or optical readouts can be selected for use in conjunction with the beam-oriented pixellated scintillators and can include, for example, numerous charge coupled devices (CCDs), position sensitive or multi-anode photomultipliers (MAPMT), MCP-PMTs, avalanche photodiode arrays (APDs), and the like. In one embodiment, for example, a radiation detector device of the present invention can include high frame rate and/or internal gain CCD, such as an electron multiplying CCD (EMCCD), coupled with a beam-oriented pixellated scintillator.

In another embodiment, a detector device of the invention can include an element or device for affecting or selecting photons reaching the scintillator, such as a collimator. Collimators included in a device of the present invention can include, for example, single or multiple pinhole collimators, convergent or divergent multihole collimators, coded apertures and the like. Methods and devices of the present invention can further include numerous radiation sources, such as a radioactive source, electromechanical device (e.g., X-ray generator device), radiopharmaceutical agent, and the like.

In yet another aspect, the present invention provides an X-ray imaging device. The device includes an imaging plate comprising a beam-oriented pixellated scintillator having an array of pixels, each pixel of the array having a pixel axis oriented to substantially match a predetermined illumination direction of a radiation beam reaching the pixel, with at least one of the pixels having an axis that is at an angle relative to another pixel axis of the array. The X-ray imaging device of the invention further includes an X-ray source spaced from the imaging plate.

In one embodiment, the X-ray source and imaging plate can be spaced from each other such that the focal point of the pixels of the array and a focal point of the X-ray source are substantially coincident. The device can further include a means for moving and/or rotating an object that is being imaged and placed between the imaging plate and the X-ray source. For example, the X-ray source and the imaging plate can be rotatable about the imaged object while maintaining substantial coincidence between the focal point of the pixels and the focal point of the X-ray source. The X-ray imaging device can include one or a plurality of imaging plates, with each imaging plate including a beam-oriented pixellated scintillator.

In another aspect, the present invention provides a method of fabricating a beam-oriented pixellated scintillator. The method includes forming a plurality of grooves in a slab of scintillator material so as to form an array of pixels, each pixel of the array having a pixel axis oriented to substantially match a predetermined illumination direction of a radiation beam reaching the pixel, at least one of the pixels having an axis that is at an angle relative to another pixel axis of the array. Formation of grooves and pixels of the scintillator can be accomplished using a variety of techniques and can include, for example, laser ablation or laser micromachining techniques.

In yet another aspect, the present invention provides a method of performing radiation detection. The method can include providing a radiation detector including a beam-oriented pixellated scintillator of the invention, such as a scintillator having an array of pixels, each pixel of the array having a pixel axis oriented to substantially match a predetermined illumination direction of a radiation beam reaching the pixel, at least one of the pixels having an axis that is at an angle relative to another pixel axis of the array; and positioning a target (e.g., object, patient, etc.) within a field of view of the radiation detector as to detect emissions from the target or absorption by the target.

Emissions detected according to the methods of the present invention can include, for example, gamma-rays, X-rays, electrons, and the like. Emissions detected include where the target itself is a source of detectable signal, as well as where a radiation source separate from the target is included and energetic photons emitted from the source pass from the emission source to the detector, with the target positioned between the detector and the emission source. Thus, in one embodiment, the radiation detectors can be used for imaging applications including medical imaging, such as in a method of performing X-ray imaging, single photon emission computed tomography (SPECT), and the like. In certain embodiments, an imaging method can include injecting or otherwise administering a patient with a detectable label and, after a sufficient period of time to allow localization or distribution of the label, placing the patient within the field of view of the detector. Thus in some embodiments the target includes a patient (e.g., human, animal, etc.) or a portion of the patient.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 5A through FIG. 5D illustrate radiation detection devices according to several embodiments of the present invention.

FIG. 6A and FIG. 6B illustrate a laser beam delivery system and fabrication of a beam-oriented pixellated scintillator according to another embodiment of the present invention.

FIG. 7A shows the 3 mm thick beam-oriented pixellated scintillator with 250 μm pixels, and FIG. 7B shows a magnified view of the same beam-oriented scintillator.

FIG. 9A shows a histogram of energy deposition on a pixellated scintillator crystal. FIG. 9B shows comparison of the histograms of the depth of interaction of photons between continuous (e.g., non-pixellated) and pixellated scintillator crystals. Orientation of the V-shaped grooves relative to the photon source alters the depth profile. The smallest depth of interaction (DOI) is given by the curve for the pixellated face of the scintillator crystal oriented away from the source ("Pixelated crystal, reversed orientation").

DETAILED DESCRIPTION OF THE INVENTION

The present invention provides beam-oriented pixellated scintillators and radiation detectors having significantly enhanced performance characteristics, including improved spatial resolution, and having reduced and/or minimized parallax errors. A beam-oriented pixellated scintillator of the present invention includes an array of pixels separated by inter-pixel grooves, and the pixels can be oriented to form a beam-oriented array that is matched to the illumination directions of radiation beams reaching the pixels. The beam orientation of the pixels of the array significantly improves detector performance and ensures minimal parallax errors in localizing high-energy photon events (e.g., gamma-rays, etc.).

Some previously available designs of ring PET cameras orient individual scintillators toward a central area. These, however, include general orientation of each entire scintillator (e.g., scintillator panel) toward a generalized target area. The target object and positron emitters in the object are distributed over a relatively large portion of the field of view (e.g., diameter of the ring of detectors), so that most of the radiation reaching the scintillator is at an angle relative to an axis (e.g., pixel axis) of the scintillator, and parallax errors are a considerable source of spatial resolution in these cameras. See, e.g., U.S. Pat. No. 7,217,928. Similarly, some previously available x-ray CT scanner configurations include two-dimensional arrays of individual detectors placed on an inner diameter of a ring. While an axis of the scintillators in such configurations may be pointed toward a focal spot of the x-ray tube in an azymuthal direction, pixel axes in a scintillator panel (e.g., even where pixilated scintillators are used) are longitudinally parallel, with pixel axes progressively deviating from beam direction/angle as progressing further from the center of the scintillator panel in a longitudinal direction. See, e.g., U.S. Pat. Nos. 5,757,951; 6,944,263; 5,510,622.

Figure 1:
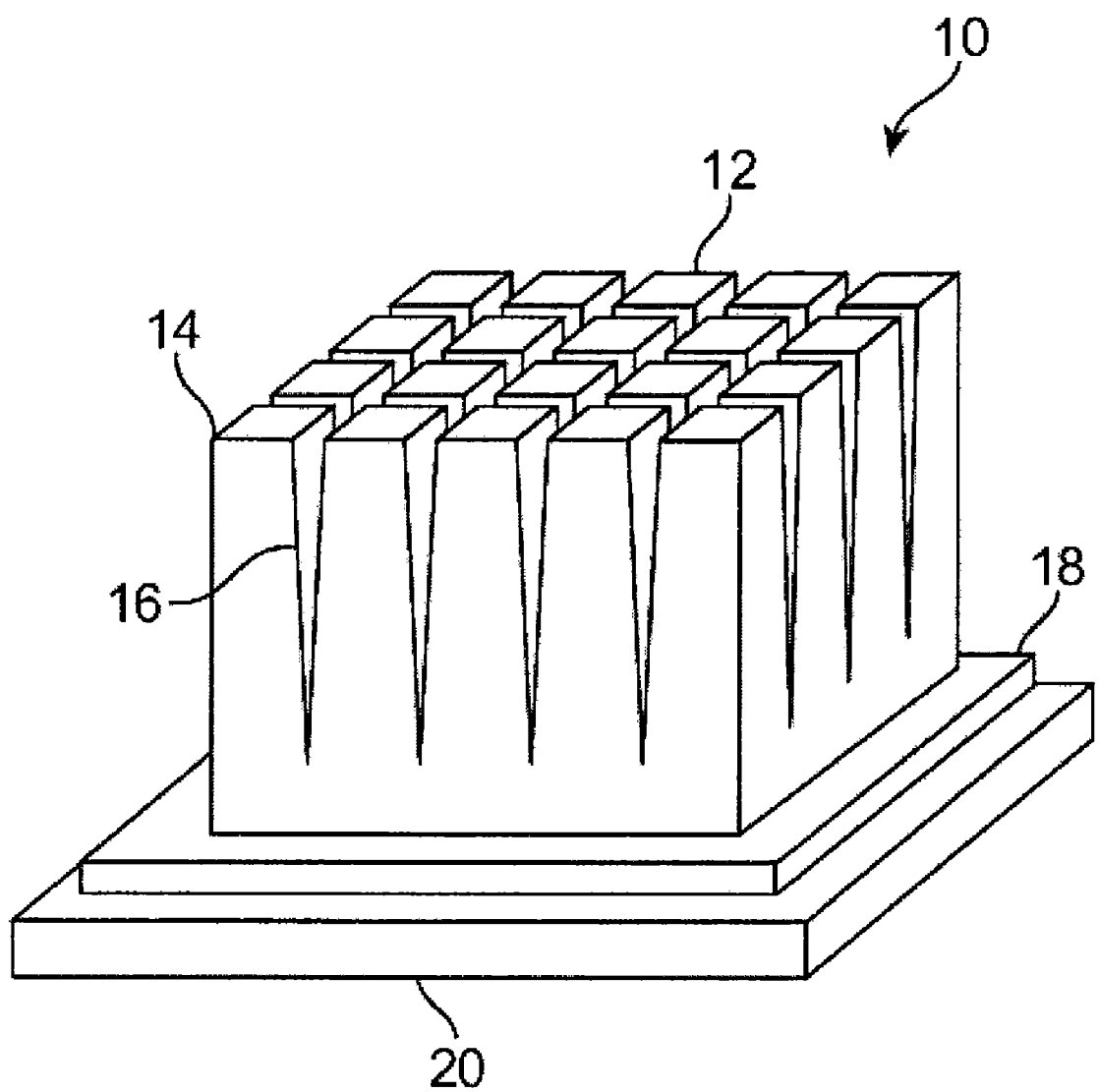
FIG. 1 illustrates a radiation detector having a beam-oriented pixellated scintillator according to one embodiment of the present invention.

Referring to FIG. 1, a radiation detector according to one embodiment of the invention is illustrated. The detector 10 includes a beam-oriented pixellated scintillator 12 having an array of pixels 14. Pixels of the array are separated by inter-pixel grooves 16, which can include a variety of shapes and dimensions. Inter-pixel grooves 16 can extend through the entire thickness of the scintillator 12 or partially through the scintillator 12, as shown in FIG. 1. The scintillator 12 can be disposed on a substrate 18 (e.g., transparent substrate) and optically coupled to a photodetector 20. The base side of the scintillator 12 refers to the side of the scintillator 12 facing the substrate.

Figure 2:
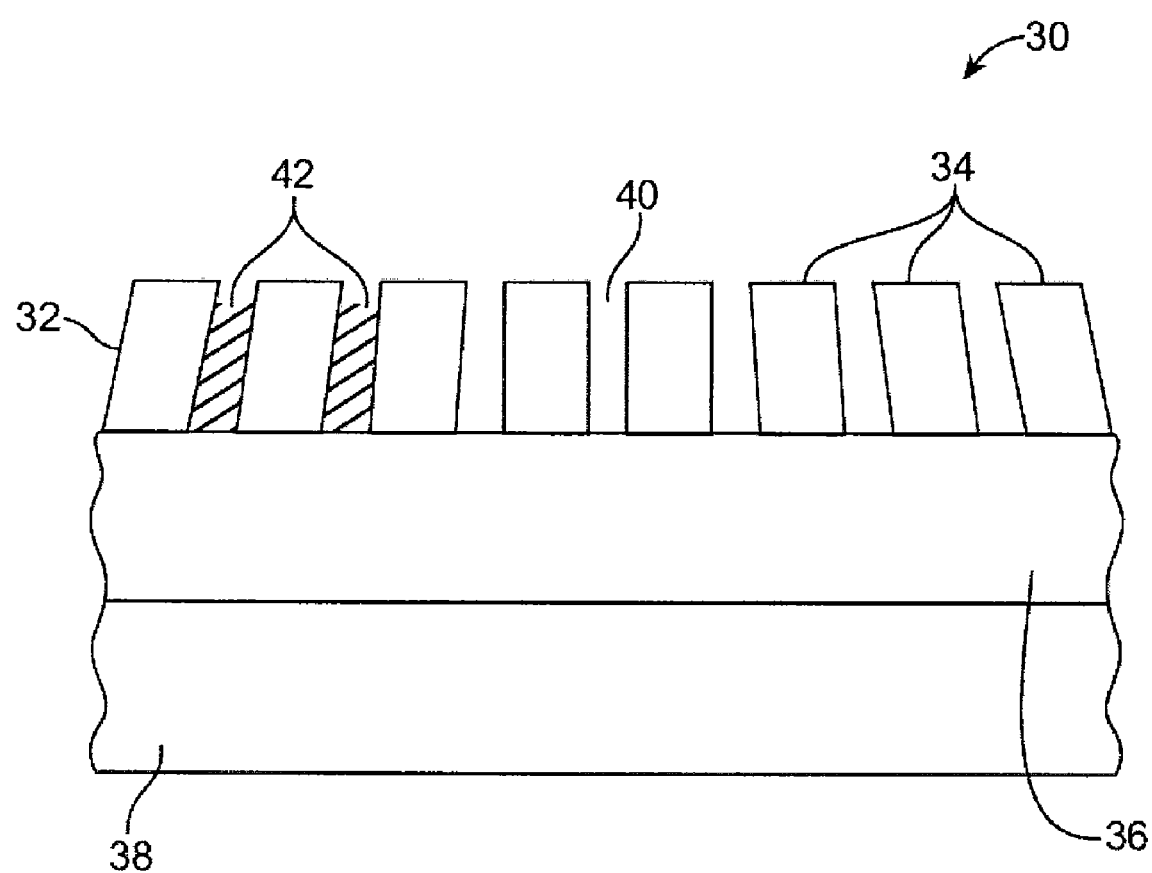
FIG. 2 shows a radiation detector and beam-oriented pixellated scintillator according to another embodiment of the present invention.

A radiation detector of the present invention is further illustrated in FIG. 2. The detector 30 includes beam-oriented pixellated scintillator 32 having an array of pixels 34, with the scintillator 32 disposed on a substrate 36 and optically coupled to a photodetector 38. As shown in FIG. 2, inter-pixel grooves 40 separating pixels 34 of the array can extend entirely through the thickness of the scintillator 32, such that pixels 34 of the array are both optically and physically independent. Inter-pixel grooves 40 can be left empty or can contain a material 42 deposited therein.

Pixels are typically optically independent, such that light photons traveling along the pixel length do not substantially pass between adjacent or neighboring pixels. The depth of the grooves or extent to which the grooves extend through the thickness of the scintillator slab can vary in different embodiments. In some instances, grooves defining a pixel can extend entirely through the thickness of the scintillator material such that the pixel is both optically and physically independent relative to other pixels of the array (see, e.g., FIG. 2). A scintillator slab can be disposed on a substrate prior to pixel formation such that removal of scintillator material in formation of the inter-pixel grooves leaves individual pixels disposed on a substrate surface. In another embodiments, grooves may extend only partially through the thickness of the scintillator such that adjacent pixels form a continuous pixel array (see, e.g., FIG. 1). For example, grooves may extend partially through the scintillator slab, but no farther than 200 μm from the uncut surface of the slab or the surface of the slab opposite the slab surface into which the groove is formed. A monolithic array or scintillator, for example, will include a plurality of pixels defined by inter-pixel grooves extending partially through the thickness of the scintillator.

Thus, in one particular embodiment, a scintillator of the invention includes a monolithic scintillator. At least some pixels of a monolithic scintillator or array can form a continuous array, rather than a collection of pixel elements that need to be individually assembled so as to form a robust array. For assembly of individual or non-continuous pixels to form an array (e.g., non-monolithic array) see, for example, U.S. Pat. No. 6,798,717.

Figure 3:
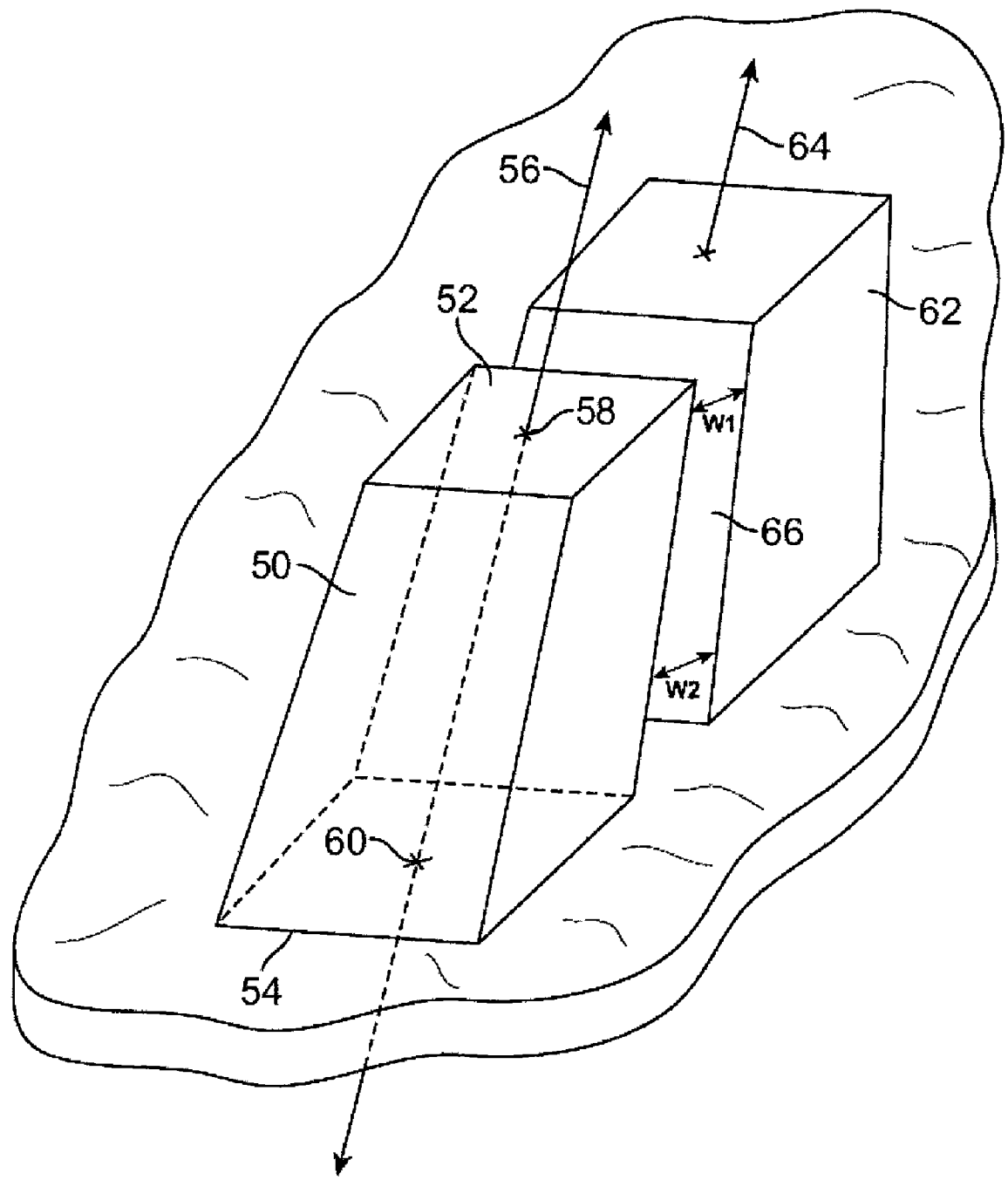
FIG. 3 illustrates pixels of a beam-oriented pixellated scintillator according to an embodiment of the present invention.

FIG. 3 illustrates beam-oriented pixellated scintillator of the present invention disposed on a substrate, showing orientation of individual pixels of an array. Pixel 50 includes a top face 52 and a bottom face 54 on opposed surfaces of the scintillator. In operation a device including the scintillator, light photons will exit the pixel through at least one of the faces 52, 54, e.g., toward an optically coupled photodetector. The pixel 50 includes a pixel axis 56, which is represented as a line passing through the geometric centers 58, 60 of the opposing faces 52, 54. Similarly, pixel 62 includes a pixel axis 64 passing through the geometric centers of opposing top and bottom faces of the pixel 62. Relative spacing of adjacent or neighboring pixels 50, 62, or pixel "pitch", is measured by the center to center distance of the pixel axes 56, 64. The pixel 50 is additionally separated from adjacent pixel 62 by an inter-pixel groove 66. The inter-pixel groove 66 can include a substantially parallel-sided groove, where W1 and W2 are substantially the same. In another embodiment, the groove 66 is a wedge or V-shaped groove, with W1 being greater than W2. Inter-pixel grooves are not limited to any particular shape or conformation.

Orientation and/or angle of the pixels of the array can vary with respect to other pixels of the array. For example, a pixel can be oriented such that the pixel axis is generally orthogonal with respect to a surface on which it is disposed (e.g., planar surface of a substrate), or the pixel axis can deviate from such an orthogonal orientation. Pixels of an array of a beam-oriented scintillator will include a plurality of angles or orientations such that a given pixel of the array will have a pixel axis that is at an angle relative to at least one other pixel axis of the array, or a plurality of pixel axes of the array. Accordingly, pixels of the array can be oriented to form a beam-oriented array that is substantially matched to the illumination directions, predetermined or expected, of radiation beams reaching the pixels.

Pixels of a beam-oriented pixellated scintillator of the present invention are not limited to any particular pixel shape or pattern of pixels of an array or plurality of arrays. For example, a scintillator of the invention can include pixels formed by substantially equidistant parallel grooves defining a 2-dimensional array along orthogonal x, y axes, with substantially square pixel faces and substantially equidistant centers. The pixel patters can also include non-equidistant centers and/or non-parallel grooves and may include, for example, a polar coordinate system, spiral configuration, with equal or unequal distances between successive grooves, and the like. Pixels can include a variety of shapes including, without limitation, square, rectangular, rhomboidal, triangular, or hexagonal shapes.

In certain embodiments, a radiation detector of the invention can include an element or device for affecting or selecting photons reaching the scintillator, such as a collimator. For example, various radiation imaging techniques, such as single photon imaging (e.g., planar, SPECT, etc.), make use of a collimator positioned between a radiation source and a scintillator of the detector. The collimator selectively allows energetic photons (e.g., gamma-rays, X-rays, etc.) having certain trajectories and illumination paths aligned with holes of the collimator to pass through to the detector, while blocking and/or absorbing other photons. Various collimators are known and will be suitable for use in radiation based imaging and detection according to the present invention and can include, for example, pinhole collimators, multiple-pinhole collimators, parallel-hole collimators, convergent and divergent multi-hole collimators, and the like. Collimators can additionally include coded apertures, which allow radiation beams having a given trajectory and illumination path, or a single point in an imaged object, to be simultaneously detected by two or more areas or regions (e.g., arrays) of the scintillator. A beam-oriented pixellated scintillator coupled with a collimator can have regions or arrays of pixels, where pixels of the array are oriented such that the pixel axes substantially match the illumination direction of radiation beams passing through the collimator and reaching the pixels. It will be recognized that while a pixel axis for each pixel can be well defined, the illumination direction of a radiation beam that will illuminate a particular pixel will include a radiation beam angle having a small amount of spread or variation around an average value due, for example, to the finite size of collimator holes, scatter effects in the collimator, and the like.

Figure 4:
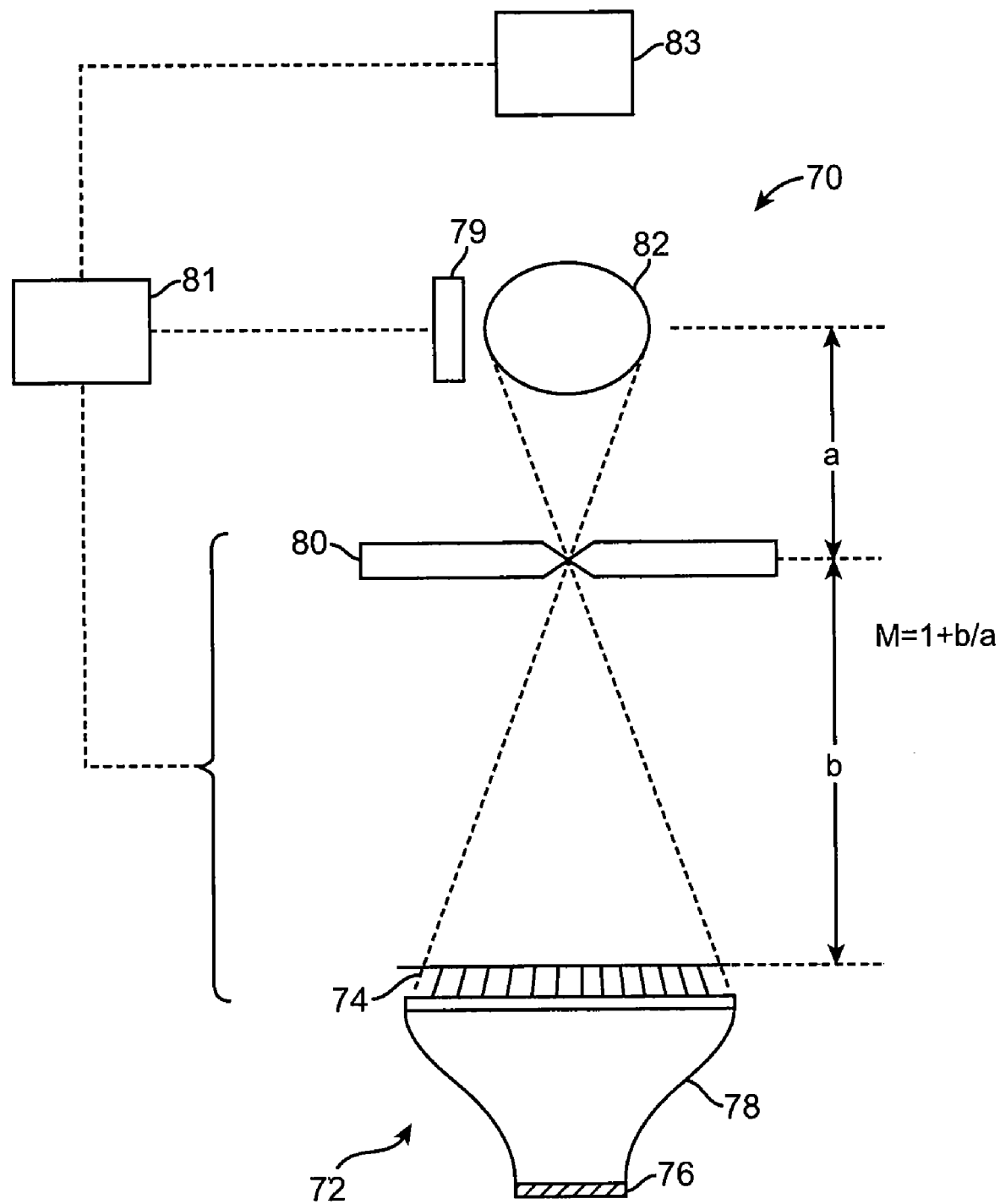
FIG. 4 illustrates a radiation detection device having a beam-oriented pixellated scintillator according to another embodiment of the present invention.

FIG. 4 illustrates a radiation detector according to one embodiment of the present invention. The detector 70 includes an imaging plate 72 having a beam-oriented pixellated scintillator 74 optically coupled to a photodetector 76 (e.g., CCD, EMCCD, etc.). In the illustrated embodiment, the scintillator 74 is coupled to the photodetector 76 via a coupling path 78. The detector 70 further includes a collimator 80. As illustrated, the collimator 80 can include, for example, a pinhole collimator having single pinhole that projects an image 82 of an object onto the scintillator 74. The pixels of the scintillator 75 are oriented so that the axis of each pixel is beam-oriented or points to the pinhole. As set forth above, such a beam-oriented arrangement of the pixels of the scintillator 74 can substantially reduce or minimize parallax errors.

In one embodiment, the scintillator is coupled to photodetector via a fiber optic taper coupling path. It will be recognized, however, that a variety of coupling means can be used for optically coupling the scintillator to other components of a device, such as a photodetector. For example, the optical coupling path can include a direct contact to the photodetector, a fiber optic link, a lens system, mirrors and prisms, and the like. An object 82 imaged by the detector can be stationary or be moved during the imaging process (e.g., via means 81). The detector can include, for example, a stage 79 (e.g., plate) onto which the object is positioned for imaging, and/or can include a gantry or movable assembly onto which the radiation source (e.g., radiation source 83) is coupled or mounted. Several detectors of the invention could be assembled (e.g., in a ring configuration) to form a high performance, high-throughput imaging system (e.g., small animal SPECT system).

FIG. 5A through FIG. 5D illustrate various embodiments of radiation detectors including collimators positioned between an imaged object 90 and a beam-oriented pixellated scintillator. Dashed lines show radiation beam illumination directions, with the pixels of the scintillators oriented to substantially match the radiation beam illumination directions. FIG. 5A shows a beam-oriented pixellated scintillator 92 coupled with a single pinhole collimator 94, with the intersection point of the axis of the pixels of the scintillator 92 located at the pinhole. In another embodiment, a detector of the invention includes a beam-oriented pixellated scintillator 96 coupled with a multiple pinhole collimator 98 (FIG. 5B). Thus, the scintillator 96 can include a plurality of regions or arrays of pixels, where the pixels of individual regions can include different intersection points for the pixels' axis. As illustrated in FIG. 5B, the scintillator 96 includes regions of pixels separately beam-oriented to pinholes of the collimator 98. In another embodiment, a detector includes a beam-oriented pixellated scintillator 100 and a convergent hole collimator 102 (FIG. 5C), with the intersection point of the axis of the pixels 100 positioned in front of the detector or a side of the collimator 102 opposite the side of the collimator 102 facing the scintillator. Individual regions or arrays of pixels are oriented to match illumination directions of radiation beams passing through the holes of the collimator 102. FIG. 5D illustrates a detector having a beam-oriented pixellated scintillator 104 and a divergent hole collimator 106, with the intersection point of the axis of the pixels 104 on a side of the scintillator 104 opposite the side of the scintillator 104 facing the collimator 106.

Pixellation of the scintillator material, including micromachining or ablation of the scintillator material to form the inter-pixel grooves, can be accomplished by a variety of methods. In one embodiment, pixellation and ablation of the inter-pixel grooves is accomplished by laser micromachining or laser ablation techniques. Laser ablation pixellation may be desired, for example, as the desired pixel size and/or width of the inter-pixel grooves decreases, as laser micromachining techniques described herein permit formation of inter-pixel grooves that are narrower than those grooves typically formed by conventional or previously known methods. For example, while known saw cutting methods (e.g., diamond saw cutting) typically form grooves about 200 μm in width, the laser ablation methods described herein can produce narrower grooves, including grooves 10 to 70 μm in width. Additionally, since ablation of larger inter-pixel grooves will remove more scintillator material during the fabrication process, decreased groove width allows for retention of a larger amount of effective fractional surface area of the scintillator material thus also allowing for substantial gains in detector sensitivity. Table I illustrates estimated scintillator sensitivity for various pixel sizes formed by conventional ablation methods having 200 μm wide grooves compared to those formed by laser ablation methods of the present invention 50 μm wide grooves, showing substantial gains in sensitivity in scintillators with the narrower grooves formed by the laser ablation methods. Additionally, the flexibility of the laser ablation technique more easily permits customization of the micropixellated slab to match the selected configuration of a detector device into which it is incorporated, such as a configuration including a collimator.

TABLE I

| Gain in sensitivity using the laser pixellation compared to current methods. | | | |
|---|---|---|---|
| Pixel Size (mm2) | % Sensitivity 200 μm | % Sensitivity 50 μm | % Gain in Sensitivity |
| 1 × 1 | 69 | 90 | 31 |
| 0.75 × 0.75 | 62 | 88 | 41 |
| 0.5 × 0.5 | 45 | 83 | 84 |
| 0.25 × 0.25 | 31 | 70 | 225 |

A laser delivery system of the present invention is described with reference to FIG. 6A and FIG. 6B. The system 120 includes a laser assembly 122 including at least one laser 124 for delivering a laser beam 126 to a scintillator slab 128 and ablating or forming grooves 130, and therefore pixels, on a surface of the scintillator slab 128. The scintillator slab 128 can be placed on a stage 132 for holding and/or positioning, angulating the slab 128 with respect to the delivered laser beam 126. The system 120 further includes a control unit 134 for selecting and controlling the delivered laser beam 126, as well as the relative translation and angulation of at least a component of the laser beam assembly 122 (e.g., laser, laser beam, etc.) and the stage 132 having a scintillator slab 128, and selecting the groove formed on the scintillator slab 128. The laser delivery system 120, including the control unit 134, can include, for example, a wide variety of customized, proprietary and/or commercially available electronics, computers or systems having one or more processing structures, a personal computer, mainframe, interface, or the like, with such systems often comprising data processing hardware and/or software configured to have algorithms and/or instructions to implement any one, or combination of, the method steps described herein. Any software will typically comprise machine readable code of programming instructions embodied in a tangible media such as a memory, a digital or optical recording media, optical, electrical, or wireless telemetry signals, or the like, and one or more of these structures may also be used to transmit data and information between components of the system in any of a wide variety of distributed or centralized signal processing architectures.

In one embodiment, fabrication methods of the present invention can be performed using an excimer laser delivery system. Laser beam energy at the target can be in the range of about 200 to 350 mJ, pulse duration of about 10 to 100 ns, and pulse frequency in the range of about 50 to 500 Hz. The number of pulses at each point can be varied (e.g., about 100 to 7000) to achieve the required groove depth during a single pass of the laser beam. The resulting groove depths and profiles can be examined or studied, for example, using an optical microscope and the resulting data used to select a set of parameters that allow deep etching with minimum inter-pixel spacing. Optimized process parameters can produce very high aspect ratios (e.g., etch depth to gap width) typically ranging from about 70 to about 90, while maintaining sharp edge definition.

In one exemplary embodiment, ablation of a scintillator composition (e.g., CsI(Tl)) was performed using a KrF ($\lambda$=248 nm) excimer laser. The laser output energy can be set, for example to 300 mJ and the pulse repetition rate to 200 Hz. A specifically cut mask (e.g., mask having a 1.2×19 mm rectangular slot) can be mounted in front of the port beam so as to produce the desired line pattern in the scintillator slab. In one embodiment, optics consisting of attenuators, mirrors, high quality spherical lens (e.g., 75 mm focal length) can be used to image the rectangular slot onto the target with a de-magnification ratio (e.g., 36:1). For etching pixel patterns, the scintillator slab can be mounted on a high-precision x, y scanning table, with the motion of the table synchronized with the laser output to ensure that each spot along the scanned line receive an identical number of pre-determined pulses. After cutting lines in one direction with a single pass for each line, the scintillator slab can be rotated (e.g., 90 degrees) and the ablation process repeated to form the required pixel pattern. Such a beam delivery system can produce the required energy densities on the scintillator targets with a minimum cost. In certain embodiments, energy loss can occur due to the non-optimized beam optics in this system. For example, laser-to-substrate (scintillator) energy efficiency with one system was estimated at about 11%, indicating that about 90% of the laser energy was not used for etching purposes.

Using the excimer laser system having a configuration according to the above described embodiment, groove depths can be varied linearly with the number of pulses, while maintaining a given laser energy density and width of the beam on the target. This is an important aspect of this laser configuration as it indicates that the wedge shaped laser beam delivers enough energy at the bottom of a groove (e.g., 3 mm deep), or portion of the groove most distal to the laser, to produce ablation of the scintillator material. In alternate embodiments of a laser beam delivery system where the energy density falls short at the distal portion of the groove, instead of ablation the energy would be transferred to the scintillator material (e.g., CsI lattice), resulting in local heating and/or possible cracking and destabilizing of the scintillator material structure, which is undesirable. A solution to continue deeper etching in such a case can be to increase the width of the mask coupled with the laser so as to increase the width of the beam on the target (e.g., scintillator slab) thereby additionally producing wider grooves. Changing mask width can correspondingly change both processing time and groove dimensions. For example, in one embodiment etching grooves in CsI(Tl) scintillator slabs to a constant depth of 3 mm using masks of varying widths (e.g., about 1.2 mm to about 1.8 mm) produced grooves with varying widths (e.g., about 32 µm to about 54 µm, respectively). Furthermore, the corresponding number of pulses required to attain a desired depth (e.g., 3 mm) generally decreases with increasing mask width, and increasing mask width can also reduce processing time. Preferred mask width will vary from 0.4 mm to 2.8 mm for beam delivery system demagnification of 40 and will vary according to the demagnification used.

In another embodiment, etch rate can be increased or enhanced by increasing the laser pulse frequency. In one example, laser frequency increased from about 100 Hz to about 200 Hz correspondingly increased etch rate by about a factor of two without significantly affecting the groove width (e.g., about a 4% increase in groove width going from about 100 Hz to about 200 Hz). A set of laser process parameters according to one embodiment of the present invention is set forth in Table II, though it will be recognized that various configurations are available and can be selected in part based on a particular application (e.g., scintillator material, thickness, desired groove parameters, etc). The number of pulses at each point can also be varied and can be selected based, for example, on the thickness of the scintillator material being processed as well as other factors. In one embodiment, about 1400 pulses were delivered to produce about 3 mm deep cuts over an about 0.5 mm width, corresponding to a linear etching rate of about 1 cm/2.3 minutes. In one embodiment, laser process parameters can include, for example, energy density of about 30 mJ/cm$^2$ to about 3 J/cm$^2$; pulse frequency of about 50 Hz to about 500 Hz; pulse duration of about 10 fs to about 100 ns; mask width can be about 0.4 mm to about 2.8 mm

TABLE II

A set of laser process parameters selected for CsI(Tl) laser pixellation.

| Laser Parameter | Energy Density (mJ) | Pulse Frequency (Hz) | Pulse Duration (ns) | Mask Width (mm) |
| --- | --- | --- | --- | --- |
| Value | 300 | 200 | 100 | 1.4 |

Scintillator slabs of various composition, size and dimensions can be processed according to the methods of the present invention and to form a beam-oriented pixellated scintillator. In one embodiment, scintillator slab to be subject to pixellation can be generally square or rectangular in shape and measure about 2.5×2.5 cm$^2$ in area and having a thickness ranging from about 0.5 mm to about 1.5 cm. Though it will be recognized that the present invention is not limited to any particular size, shape or dimension of slab of scintillator material that can be processed according to the present invention.

Scintillator material can be optionally processed and/or modified prior to or subsequent to pixellation. For example, a scintillator material can be processed in order to refine surface conformation, such as to even the scintillator surface, remove projections/recesses present on the scintillator surface, modify thickness, etc. In some instances, for example, scintillator processing can be preformed in order to enhance adhesion of a coating or layer deposited thereon (e.g., protective layer, reflective layer, etc.). Non-limiting examples of processing include mechanical polishing, etching (e.g., chemical, laser, etc.), sandblasting, cleaned (e.g., plasma cleaning procedures), and the like. In one example, scintillator crystals cut from a boule were subjected to mechanical polishing to a surface finish of about 1 μm.

Furthermore, scintillator material can be optionally coupled with or disposed on a substrate prior to or subsequent to pixellation. A coupled substrate can provide mechanical support and/or affect scintillation properties or performance of a scintillator. Exemplary substrates can include, e.g., carbon, beryllium, boron, carbide, aluminum substrates, and the like. The substrate surface onto which the scintillator is disposed is generally a substantially flat or planar substrate surface, though may be non-planar or curved in some instances. In some instances, the scintillator is disposed directly on a surface of a photodetector (e.g., via coupling material, glue, etc.). Thus, in some embodiments a substrate comprises a photodetector. In one embodiment, scintillator samples can be bonded to an alumina substrate (e.g., about 0.5 mm thick alumina substrate) prior to pixellation. The alumina substrate provides mechanical support to the pixellated substrate once the scintillator material is etched, facilitate handling and manipulation of the pixellated scintillator and due to its white surface serves as a reflector to maximize the light collection efficiency of the scintillator.

Figure 7:
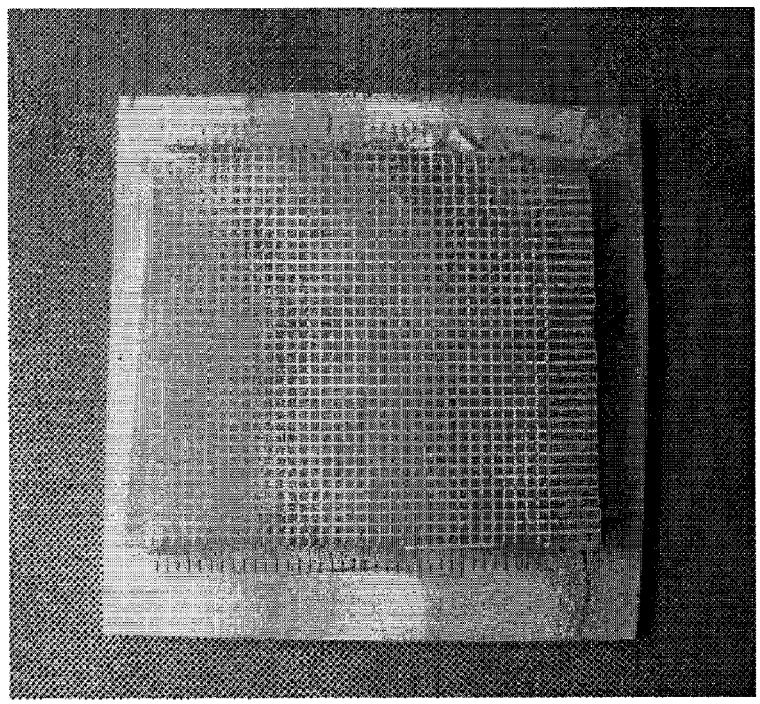
FIG. 7A and FIG. 7B illustrate a beam-oriented pixellated CsI(Tl) scintillator crystal mounted on a alumina substrate (5.5 mm), having a reflector coating or paint, and polished surface.
Figure 7:
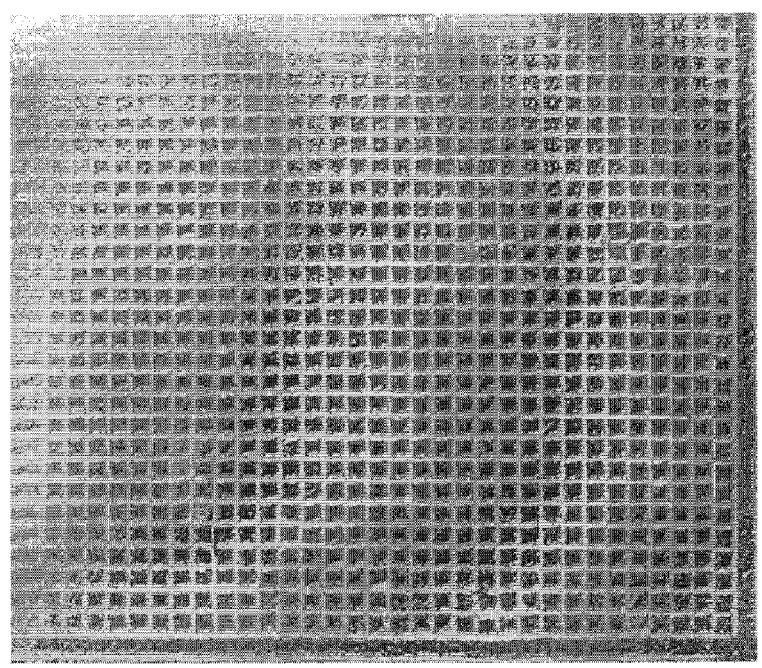
Figure 8:
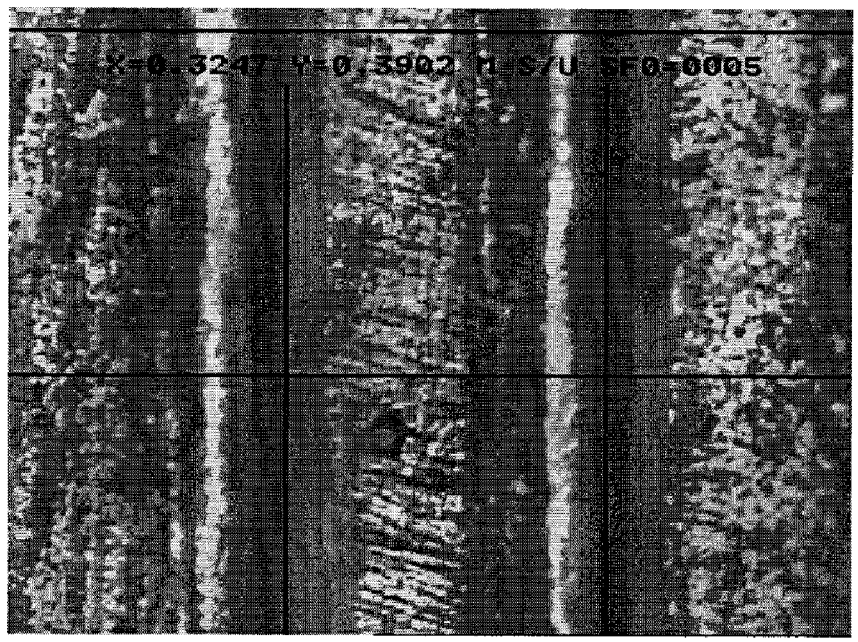
FIG. 8A and FIG. 8B show a top view (FIG. 8A) and side view (FIG. 8B) of laser ablated or laser micromachined grooves of a beam-oriented pixellated scintillator according to an embodiment of the present invention.
Figure 8:
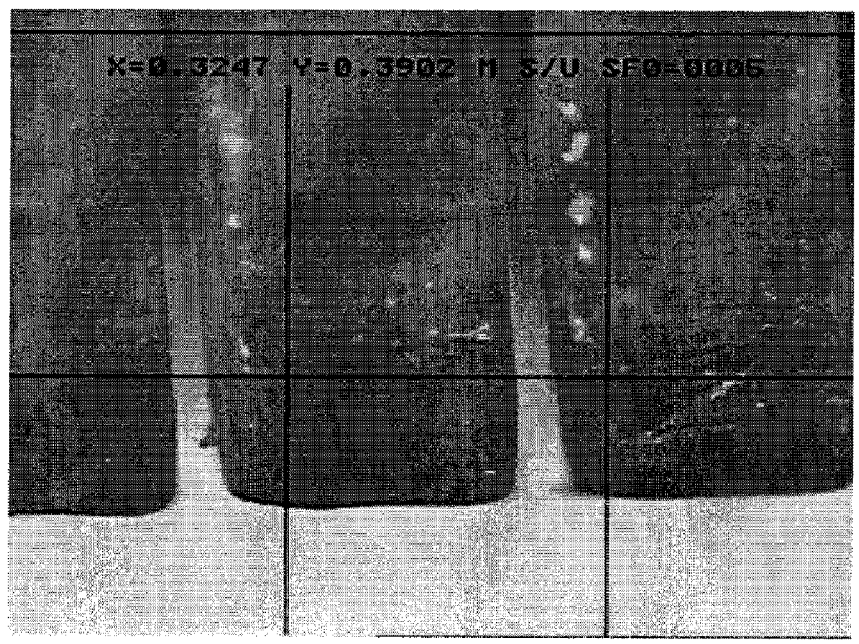

An exemplary pixellated scintillator according to one embodiment of the invention is show in FIGS. 7A and 7B and FIGS. 8A and 8B. Photographs of a sample etched with 250×250 μm$^2$ pixels are shown in FIGS. 7A and 7B and the corresponding high magnification images illustrating inter-pixel gaps of about 38 μm are shown in FIGS. 8A and 8B. Such narrow gaps with 3 mm cutting depth resulted in a high aspect ration of about 78:1, illustrating the utility of the laser ablation techniques of the present invention in forming fine pixels in a pixellated scintillator.

Another advantage of the fabrication techniques of the present invention includes the relatively short fabrication time, allowing efficient production of the pixellated scintillators. Average process time for each of the arrays can vary based, for example, on the size of the pixellated area (e.g., 2.5×2.5 cm$^2$), pixel pitch, pixel size, crystal thickness, groove depth, etc. In one embodiment, pixellation of a 500 μm thick crystals with 250 μm pixel size can be accomplished in less than about 3.2 hours, and pixellation a 3 mm thick crystal can be accomplished in less than about 19 hours, even where the beam delivery system used is not yet fully optimized for pixellation. Substantially shorter processing times can be accomplished by optimization of the beam deliver system. For example, etching shorter grooves at a time (e.g., 0.5 mm grooves at a time) and utilization of a smaller percentage of total laser power (e.g., 10%) can lead to longer processing times. Furthermore, use of a non-homogenized laser output with significant variations in laser output across the output beam can require use of a narrow mask resulting in less than optimal on-target spot size (e.g., 0.5 mm). Processing time can be reduced, for example, using a beam delivery system using an unstable resonator cavity which may produce a homogenized beam, thereby enhancing the process through put by an order of magnitude or higher compared to using a non-homogenized laser output. Thus, in one embodiment, processing time for a scintillator slab (e.g., 3 mm thick, 2.5×2.5 cm$^2$ CsI(Tl)) can be less than about 2 hours.

Processing time can additionally be reduced by increasing the energy of the beam delivery system. In one embodiment, for example, the beam delivery system results in about a 90% beam attenuation. In order to increase the scanning dimension of the laser spot, the corresponding axis of the excimer beam can be expanded onto a mask with a larger dimension (e.g., about by a factor of 2). Also, a single imaging lens (e.g., 75 mm focal length single imaging lens) can be replaced with a coated doublet to improve image quality.

In another embodiment, the excimer laser can be left unexpanded and impinging on the original mask. For example, an anamorphic imaging system can then be utilized where the scanning axis is de-magnified relative to the other axis (e.g., by 18× compared to 36×). A system of such an embodiment can include two cylindrical imaging lenses. These embodiments can produce an increase in processing throughput, e.g., by a factor of 2 or more. Furthermore, operating a higher frequency (e.g., 200 Hz compared to 100 Hz) can additionally increase (e.g., double) the laser power output with a corresponding impact on processing throughput.

The present invention further includes reconfiguring the laser cavity so as to increase gains in beam energy. Such modifications can allow for processing at reduced energy densities. Under this approach, an excimer laser is configured with unstable resonator optics and the beam deliver modified accordingly. The beam delivery will be an anamorphic design. The expected output energy from the unstable resonator cavity arrangement can be about 60% of the output with standard cavity configuration. However, the divergence characteristics of the resulting beam will be improved and allow for increased energy utilization.

In embodiments where there is a the low divergence with the modified laser cavity (see above), the non-scanned axis of the beam can be delivered by whole beam focusing with large F# optics. For example, a 0.05 mm required spot dimension can be achieved by focusing the proper laser axis with a 400 mm focal length cylindrical lens. Under such a configuration, all of the laser energy along this laser axis would pass through the mask. This is in contrast to embodiments where the mask blocks a portion of the laser beam energy (e.g., mask blocking of about 65% of laser beam energy). Maintaining the on-target fluence at the same level allows for an increase of the scanning dimension by the same factor. In one embodiment, for example, the on-target beam dimensions are about 0.05 mm×1.46 mm, compared to 0.05 mm×0.53 mm or 0.05 mm×1.04 mm in other configurations. The beam delivery required in order to achieve such a spot can use one cylinder lens in focusing mode, as discussed above, and a second imaging cylindrical lens. The second lens can image an appropriate sized mask to produce the 1.46 mm scanning dimension. In one exemplary embodiment, the second lens will have a focal length of 200 mm and a demagnification of 12×. The F# for this axis can be approximately 11. The expected increase of delivered energy will in turn enhance the throughput by a factor of 1.4× compared to that achieved under the above mentioned first alternative. Thus the minimum expected gain in throughput in such a configuration is about 5.6×.

Besides the advantages mentioned, an additional advantage of a laser having a modified laser cavity with the non-scanned axis of the beam configured for delivery by whole beam focusing with large F# optics is a significant increase to the depth of focus, which in turn allows for a reduction in the process fluence. For example, the system F# in this embodiment is approximately 40 for the narrow axis compared to about 7 or 8 in other embodiments. The excess energy can be adopted to further increase the scanned dimension of the on-target laser spot. The fractional increase in the scanned dimension can allow for enhancement of the throughput by the same factor. In one example, such a increase in scanned dimension could enhance the throughput by a factor up to about 2×, yielding an overall gain of 5.6 or a factor of 11.2×. In further addition to the previously cited advantages, laser micromachining according to the above techniques permits formation of a more robust array of pixels including, for example, formation of a monolithic pixellated scintillator, rather than a collection of separate pixel elements that need to be each individually assembled on a substrate to form a functioning array.

The present invention further includes modifying laser beam system optics so as to improve or increase the stability and/or structural integrity of the scintillator material of the fabricated pixellated scintillator. Stability of the array can become an issue in laser ablation of the scintillator material as the size of formed pixels decreases in size including, for example, small pixels in the range of 250 μm and smaller. One factor that can lead to decreased pixel array stability is excessive laser power being delivered to the neighboring pixels. For example, additional power can arise from secondary energy lobes in the beam surrounding the primary beam. Such secondary energy lobes can be a result of laser diffraction at the mask edge. Stability of the pixel array can be improved or increased, for example, by modifying or improving the optics and/or focusing the beam impinging on the scintillator material.

The above laser ablation or laser micromachining methods for fabricating a beam-oriented pixellated scintillator primarily include a single laser forming an inter-pixel groove in a single pass. In another embodiment, however, fabrication can include passing multiple laser beams (e.g., dual beams) over a scintillator slab to form or ablate a groove. For example, fabrication can include dual laser beams to cut the scintillator substrate while minimizing or reducing thermally induced fractures and related damage. Since some micro-scale damage may not be entirely avoidable during the laser machining process, an additional laser beam can be utilized for remedial purposes. The power density and position of the second beam relative to the surface of the scintillator being ablated can be varied to control the melt, for example, by using the second beam's eccentricity to control energy flow, thin surface layers can be heated to remove (or heal) flaws to improve strength, as well as to control microstructural changes at a local level. In one embodiment, a first scoring or scribing laser operating at a relatively low power is aimed at a location slightly in advance of a second cutting laser. The low power setting and relative positioning of the first laser are tailored to induce a groove in the surface that serves as the initial cut. In this fashion, the available power of the laser is economically used to control both the cutting and any premature fractures at the end of the machining cycle.

The inventive fabrication techniques further include smoothing or otherwise refining the surfaces of the array (e.g., pixel surfaces, groove surfaces, etc.), either prior to, during or subsequent to the laser ablation process. For example, scintillators materials often have a relatively low melting point (e.g., CsI(Tl) has a melting point of 621 degrees C.) and laser ablation of these materials typically results in an instantaneous evaporation of the ablated material, resulting in smooth pixel surfaces. Imperfection in the pixel surfaces and grooves, however, may be present in some instances including, for example, formation of tiny balls of scintillator material (e.g., balls of CsI) due to the surface tension of the molten material that does not evaporate. Thus, the present methods can further include steps of cleaning or removing debris that can occasionally be present in the areas surrounding the pixels. Such steps may be desired, for example in order to ensure the proper coating of additional layers and coatings (e.g., layers of reflective material, protective coatings, etc.) and pixel-to-pixel uniformity of performance, smooth the cut surfaces, and/or increase light output of the pixellated scintillator. In one embodiment, smoothing or refining of surfaces of the array can include mechanically or otherwise (e.g., chemical polishing) polishing array surfaces. The practicality of mechanically polishing can decrease in some situations such as where the detectors have a large number of closely spaced and/or small pixels. Thus, the methods of the invention can in some embodiments include blowing a dry gas such as nitrogen or argon through a groove while it is being cut. Chemical polishing can also be employed. Various combinations of chemicals and other factors (e.g., temperature) can be used for polishing scintillator surfaces. In one embodiment, chemical polishing includes treatment with $CuCl_2$, followed by $FeCl_3$.

Additional layers or coating can further be deposited on one or more surfaces of a pixellated scintillator. Additional coating may be desired, for example, in order to enhance the light collection properties and efficiency of the scintillator, prevent cross-talk between pixels or spreading of inter-pixel light, protect the scintillator from moisture, mechanical, or other damage during handling and/or use of the scintillator. In one embodiment, a reflective material can be deposited on at least a portion of the pixellated scintillator. Numerous methods and techniques can be used for depositing additional layers. In one example, a low refractive index material (e.g., SiO) can be deposited on top of the pixellated scintillator. Other examples include formation of a PTFE (polytetrafluorethylene) power reflector, as well as the use of various commercially available reflector coatings or paints (e.g., No. BC 622A, available from Saint Gorbain, Inc.). Deposition of coatings, such as reflective coatings, can be accomplished by a variety of techniques including, for example, by manual deposition, plasma enhanced chemical vapor deposition, and the like. In one embodiment, a thin layer (e.g., about 300 nm) of SiO with a refractive index of 1.4 can be deposited so as to surround individual pixel elements of the array, thereby forming an effective optical wave guide. The material of the reflective layer can include a refractive index lower than that of the scintillator material, thereby improving characteristics of the scintillator, such as improved light channeling. In one example, SiO ($n_{SiO}$=1.4) is deposited on a CsI(Tl) ($n_{CsI(Tl)}$=1.8) scintillator.

In certain embodiments, after application of a reflective material (e.g., reflective paint) pixellated scintillators can be placed inside a vacuum chamber and on a spinner to ensure more uniform distribution of the reflective material on a surface of the groove. For example, a small amount of paint can be poured on top of a scintillator, which can then be placed in a vacuum chamber that is evacuated (e.g., using a roughing pump). Removal of the air trapped within the pixel grooves can allow the reflective material to seep into the fine grooves. Once the air bubbles are removed, samples can be spun (e.g., at about 300 rpm) to remove excess paint and ensure uniformity of the thickness of the coating. Coating samples can then be left to dry and optionally subsequently subjected to further processing steps, such as surface polishing so as to open the pixels for light coupling, e.g., to a readout sensor. In one example, a layer of high index material (e.g., about 300 nm layer of $SiO_2$) can be formed on the scintillator by numerous methods (e.g., PECVD). In another example, a transparent protective coating, such as a hard coat of aluminum oxide (e.g., about 500 nm to about 1.5 µm) can be formed on the scintillator and can offer protection from mechanical damage during handling, as well as protection from moisture damage (e.g., atmospheric moisture).

Figure 9:
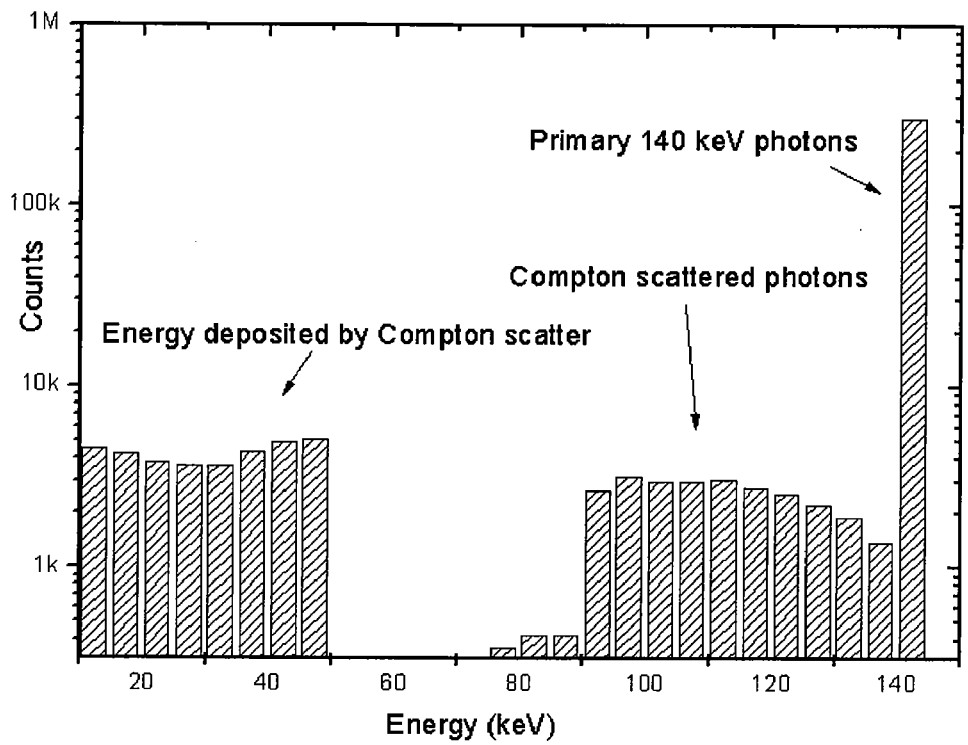
FIG. 9A and FIG. 9B show histogram analysis of scintillator crystals.
Figure 9:
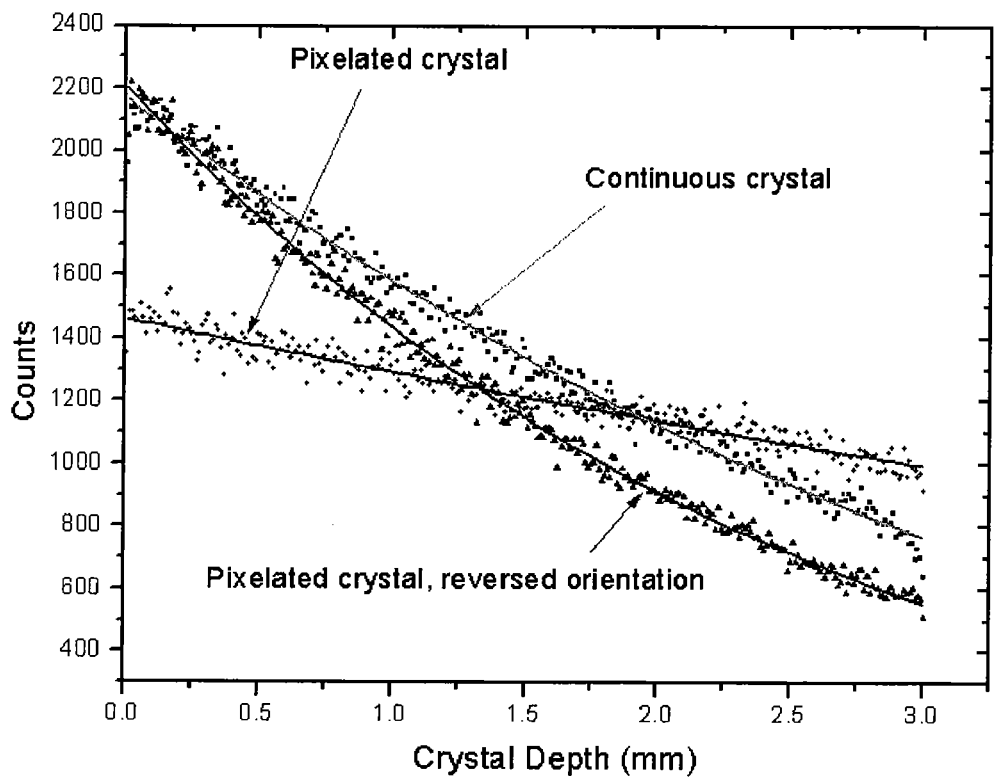

As set forth above, the pixellation techniques disclosed herein can be used to tailor the pixel pitch and orientation based, for example, on the desired performance characteristics and intended use of the device. For example, removal of scintillation material in formation of the grooves (e.g., V-shaped groove) from laser pixellation reduces the fraction of scintillator material in the slab (e.g., crystal slab), thereby reducing detection efficiency. In one example, detection efficiency was reduced from about 69% for a continuous crystal slab to about 55% for a 3 mm thick pixellated crystal with 300 µm pitch and 50 µm wide V-shaped grooves. FIGS. 9A and 9B illustrate an exemplary histogram of energy deposition into crystal pixels showing that 10% of the total detected photons undergo Compton scatter, which results in energy deposition at two or more distinct pixels. The bottom tail of the energy distribution corresponds to Compton events, where part of the photon energy is deposited in one pixel. Information from photon trajectories indicates that photons can be scattered over a few millimeters into neighboring pixels, which can result in slightly diffuse background. The non-parallel grooves from material removed from the crystal alters the depth of interaction, as illustrated in FIGS. 9A and 9B. Accordingly, the mean depth of interaction and thus potential parallax error arising from photons penetrating the crystal from oblique angles can be reduced by orienting the pixellated side of the crystal away from the radiation source, or orienting a pixel or plurality of pixels of the array such that the pixel axis or axes are oriented to substantially match the illumination direction of radiation beams reaching the pixel (s). In one example, reducing the pixel pitch to 150 µm reduces the detection efficiency to about 49%, but improves spatial resolution. It is noted that gain in intrinsic can be effected overall resolution of the imaging system, and may be limited by factors such as collimator resolution. Using the methods described herein, a desired balance between detection efficiency and spatial resolution can be selected, for example, by selecting pixel pitch and orientation/arrangement of the pixels of the array. Pixel spacing or pitch can be about 100 µm to about 1 mm, and can be selected at least partially on a desired balance between detection efficiency and spatial resolution. In one embodiment, for example, pixel pitch in the range of about 250-300 µm can be selected for better than 50% detection efficiency of 140 keV photons.

As set forth above, inter-pixel grooves can by be empty or primarily occupied by air, or can include a material deposited therein (see, e.g., FIG. 2). In one embodiment, a heavy element slurry can be introduced in the inter-pixel grooves around the individual pixels. A heavy element slurry can include, for example, elements such as lead, tungsten, tantalum, bismuth, and the like. Such deposition of a heavy element slurry may be desired, for example, in order to reduce the transfer of energy from pixel to pixel by characteristic radiation and by Compton scattered photons.

In another embodiment of the present invention, fabrication methods can further include depositing or re-diffusing a dopant into one or more of the inter-pixel grooves of the scintillator. In some instances, loss of scintillation efficiency may occur in locations at or proximate to the sites of laser ablation and may be due, for example to local annealing of scintillator material (e.g., CsI(Tl)) during laser ablation, potentially resulting in loss of dopant (e.g., Tl) from areas of ablation, such as in the ablated grooves or the pixel boundaries. As such, it may be desirable to deliver (e.g., via surface diffusion) dopant on a portion of the scintillator. For example, a thin layer of dopant can be vapor deposited on the pixellated surface and, following this deposition, the films annealed to promote dopant diffusion.

A system of the present invention further includes assemblies and components for fabricating a pixellated scintillator, e.g., by translating a scintillator slab relative to a delivered laser beam and suitable for fabrication of the desired grooves and angled pixels of the array. In one embodiment, for example, an assembly can include a stage, e.g., having a gonimeter mounted on an x,y table (see, e.g., FIG. 6A). Due to the fine scale of the pixels to be formed in the scintillator material, the precision of the x,y table, or scintillator slab holder stage, that translates the scintillator slab relative to the laser beam is important. Compared to conventional holders, an additional degree of freedom is desired to produce the grooves and angled pixels characteristic of the pixellated scintillators of the invention.

Various high precision x,y are commercially available and suitable for use in the systems or methods of the present invention. An x,y stages or tables can include a high acceleration table, or table having an acceleration of 1 g or higher. A higher acceleration may be desired for reducing processing time, particularly when a long laser beam is used to cut the scintillator slab. In one embodiment, for example, during pixellation the laser beam can continuously scan the scintillator slab rather than jogging the beam to minimize beam-positioning errors. To ensure that each spot of in the scintillator slab receives the desired predetermined number of pulses, the scanning can begin with the laser beam positioned outside of the scintillator slab. Processing time can be reduced, however, by reducing such off-target time. For example, off-target time can result in wasting laser energy and increasing process time until the entire usable beam falls on the scintillator to be cut. Since a large number of cuts are performed in some array fabrications, this off-target or "dead" time can become substantial (e.g., about 1 hour of additional processing time for a 250 µm pixels in a 2.5×2.5 cm2 scintillator slab). Processing time can be reduced and off-target time minimized by using a stage with a higher acceleration (e.g., 1 g or higher). A higher acceleration stage will help ensure that the etch rate limiting factor is the laser frequency and not the acceleration of the x, y stage, and can limit off-target or "dead" time, e.g., to less than about 5 minutes.

In one embodiment, a system of the invention includes a high-precision gonimeter, such as those commercially available (e.g., Model GON65, Newport, Inc., having an angular precision of 2 arc seconds) that can be securely mounted on an x, y table. The system can further include a sample (e.g., scintillator slab) holder that is attached to the goniometer to firmly position the scintillator slab to be cut. Scintillator slabs can be mounted on the custom designed, high precision gonimeter stage, which allows proper orientation of the sample relative to the laser beam direction to make angular cuts in the scintillator material. In one embodiment, pixellation of the scintillator in two orthogonal directions forms the required beam-oriented array. Both the x, y position of the translation table and the angular orientation of the goniometer stage can be computer controlled to achieve high precision and reproducibility in scintillator pixellation.

Thus, in one embodiment, a radiation device includes a beam-oriented pixellated scintillator mounted on a substrate, such as an optically transparent substrate (e.g., fiber optic), and laser micropixellated such that the micropixels angle so that the pixel axes point toward a radiation source, and the base side of the pixels is optically coupled to a photodetector (e.g., EMCCD) through a coupling path (e.g., fiber optic path). In another embodiment, the base side of the pixellated scintillator faces the radiation source. For example, an opaque low-Z substrate or coating may be disposed on the base side of the scintillator, with the base side facing the radiation source, and an efficient reflective coating, such as aluminum, can be further applied beneath the base of the scintillator pixels. In this "inverted" configuration, the scintillator will be oriented so that radiation enters through the base side of the pixels and light exits through the exposed tops, which can be coupled to a photodetector. Exemplary radiation-transparent substrates can include carbon, beryllium, boron carbide, aluminum, and the like.

As set forth above, a radiation detector of the invention can additionally include an optically coupled photodetector. Various photodetectors and configurations are available for use in the present invention and will depend, in part, on the type of detection device and/or the intended use of the radiation detector. For example, a radiation detector can include an optically coupled high frame-rate, electron multiplying CCD (EMCCD). Use of EMCCD's may be desired, for example, for use in high spatial resolution radiation detectors, or detectors capable of obtaining a spatial resolution better than or below 100 μm. A high frame rate EMCCD's typically has a frame rate of tens of frames per second, typically greater than about 30 frames per second (fps), and up to and exceeding 500 fps. EMCCD's can include an internal gain, for example, typically in the range of about 1-3000. EMCCD's typically provide both a quantitative improvement in performance over conventional CCDs and, due in part to their performance exceeding thresholds in frame rate and noise, offer qualitative differences as well. For example, detectors having a high frame rate EMCCD's can be capable of image acquisition of in which individual energetic photon events (e.g., gamma ray events) are spatially separated as well as enabling energy estimation of individual interaction events. The internal gain of EMCCDs permits further suppression of read noise typically associated with high frame readout CCD's. By virtue of their internal gain, EMCCD's offer sub-electron read noise even when operated at frame rates of tens of images per second and greater, allowing detectors of the invention to work in photon-counting mode.

In one exemplary embodiment, a detector of the invention includes a back thinned, 512×512 pixel EMCCD optically bonded to a 1:1 fiber optic window. Table III lists the detailed specifications of the exemplified detector. With a pixel size of 16 μm, the effective imaging area is about 8.2×8.2 mm². Specially designed coupling paths, such as fiber optic tapers, e.g., 3:1 and 6:1, can be attached to the CCD window to achieve a desired imaging area, including an imaging area of 24.5×24.5 mm² and 49×49 mm², respectively.

TABLE III

| Parameter | Specification |
| --- | --- |
| CCD Chip | E2V CCD887 BI |
| Illumination | Back Illuminated |
| CCD Format | 512 × 512 Pixels |
| Pixel Size | 16 μm Square |
| Active Area (6:1 fiber optic) | 49.2 × 49.2 mm² |
| Full well capacity | 250 ke- |
| Gain register capacity | 850 ke- |
| Readout | 16 bits; 10 MHz |
| Frame rate (full resolution) | 32 fps |
| Frame rate binned mode | Up to 520 fps |
| On-chip gain | 1 to >1000x |

TABLE III-continued

| Parameter | Specification |
| --- | --- |
| Operating temperature | −30 C. |
| Dark current | 1 e-/pixel/sec @ −30 C. |
| Read noise at 10 MHz | 35 e- (Unity gain) |
| Read noise at 10 MHz | <1 e- (Gain >35) |

Devices of the invention demonstrated EMCCD operation in photon counting mode with extremely high spatial resolution. For example, detectors of the present invention not only can distinguish primary interactions of individual γ-ray events, but also that it has the sensitivity and resolution to resolve the absorption of the secondary X-rays (e.g., Cs and I K X-rays). In one embodiment, the mean interaction length of CsI and I K X-rays ranges from about 124 to about 300 μm in CsI(Tl), but is typically about 300 μm. This high-resolution capability improved spatial resolution by rejecting the K X-ray interactions and finding the centroid of the primary interaction cluster in such image frames. In one non-limiting example, the effectiveness of this technique was demonstrated by obtaining an image of a 25 μm wide slit in tungsten using a $^{99m}$Tc 140 keV γ-ray source. The detector was operated in integration mode (one long exposure) and in photon counting mode (at 30 fps) with an internal gain set to about 200. The measured FWHM for the integration mode image was about 120 μm, which was significantly improved to about 40 μm FWHM by using the centroid approach on recorded γ-ray intensity distributions and performing sub-pixel position estimation.

Thus, the detectors of the present invention are capable of achieving large and discrete gains in spatial resolution in radiation imaging (e.g., SPECT), particularly detectors including a coupled EMCCD. Unlike conventional CCDs, EMCCDs permit very low noise, even when operated at high frame rates, which enables the photon counting mode of the detector operation. Furthermore, these detectors are capable of providing sufficient energy resolution to discriminate scattered photons from primary photons. Furthermore, parallax errors negate the gains in spatial resolution when non-parallel hole collimators are used, as is used in known detector configurations. Detectors of the present invention including a beam-oriented pixellated scintillator array have reduced parallax errors and are capable of imaging with very high spatial resolution, even when coupled with non-parallel hole collimators.

Detector Performance

Various performance parameters and characteristics of the beam-oriented pixellated scintillators and radiation detectors of the present invention can be examined or analyzed using a variety of methods. Such characterizations can be performed, for example, for quality control analysis, confirmation of desired functionality, further optimization and/or customization of the scintillators and detectors, and the like.

In one exemplary embodiment, flood fields/images, energy resolution, and efficiency parameters were analyzed by coupling pixellated scintillators to a photomultiplier tube (PMT) (e.g., Hamamatsu RS900-M64 multi-anode PMT) and exposing the resulting detector to various radionuclide sources, including sources ranging from $^{125}$I (30 keV) to $^{99m}$Tc (140 keV). In one example, analyzed detectors used customized charge division readout boards to multiplex the signals into four position-sensitive outputs, which are fed through preamplifiers and a shaping amplifier prior to digitization. For the trigger, a fast signal was picked off from the pre-amplifier and fed to a constant fraction discriminator and gate and delay generator. A 16 channel ADC board mounted on the host computer PCI bus was used to measure the data using software custom developed.

Count Rate Response Measurements

Scintillators and radiation detectors described herein include measurable count rates suitable for use radiation imaging applications. In one example, the count rate response was measured by exposing the detector to a flood field of 7.7 mCi $^{99m}$Tc 140 keV γ-rays. The source to detector distance was varied to change the flux on the detector area, and count rate as a function of flux was measured. The observed count rates as a function of flux for a 3 mm thick pixellated CsI(Tl) scintillator showed excellent linearity for well over 10,000 counts per second (cps), demonstrating that the detector dead time is negligible for imaging applications such as SPECT imaging and that the CsI(Tl) beam-oriented scintillator is capable of processing the count rates expected in realistic imaging applications.

Efficiency Measurements

Pixellated scintillators typically have a detection efficiency greater than 50%, including, for example, efficiency of about 60% to about 90%. In one example, detector efficiency for 140 keV gamma rays, was measured by placing a 2 mCi $^{99m}$Tc point source 8 cm above the center of the detector, and determining the number of events detected in an energy window corresponding to the photo peak. With the knowledge of the strength of the source and the solid angle, the efficiency of the detector module was estimated. In one embodiment, the efficiency of the pixellated, 3 mm thick, CsI(Tl) was measured to be 54%.

Energy Resolution Measurements

The pixellated scintillators will typically have energy resolution parameters suitable for use in a variety of imaging applications, such as small animal imaging (e.g., SPECT), X-ray imaging, etc. In one example, energy resolution measurements were performed using both a $^{57}$Co (122 keV) radioisotope and $^{99m}$Tc (140 keV) source. To determine the influence of scintillator thickness on resolution measurement, a 3 mm thick and a 2 mm thick pixellated CsI(Tl) scintillators were used. The pulse height spectrum was recorded with an amplifier shaping time of 4 μs to ensure complete light collection (CsI(Tl) decay time is ~1 μs) without sacrificing the count rate response. The resulting energy resolutions for both sources tested in one example were found to be about 28% for the 3 mm thick scintillator and about 32% for the 2 mm thick scintillator. Energy resolution performance was compared to that of a single crystal CsI(Tl), which shows better than 14% resolution at 140 keV.

Energy resolution parameters of a pixellated scintillator can be further optimized. For example, in some instances loss of emission efficiency may be due to the loss of dopant activator occurring during the laser ablation of the pixellated scintillator (e.g., laser ablation). In the case of CsI(Tl) scintillator material, for example, Tl activator in the CsI crystal near each groove may be lost during pixel array fabrication (see above discussion). Specifically, the laser etching process results in a local evaporation of CsI(Tl), and since the vapor pressure of Tl is almost four orders of magnitude higher than that of CsI, excessive Tl loss in the vicinity of laser-etched grooves may occur. Post-pixellation Tl dopant diffusion treatment to re-dope the crystal to ameliorate light loss and improve energy resolution of the pixellated scintillator.

Pixellated Scintillator Readout

In one example, illustration of using the pixellated scintillators for radionuclide imaging was carried out using an EMCCD photodetector assembly described above (see, e.g., Table III). Performance analysis demonstrated that the EMCCD system provides very low noise, high sensitivity, and wide dynamic range. For example, the measured dark noise at −35 C, for an internal gain of 1, was found to be 0.2 e$^-$/pixel/second. In another example, for the maximum gain of 1000, the measured noise increased to 0.3 e$^-$/pixel/second, which still is negligible. In another example, the effective read noise at 10 MHz readout speed (maximum possible speed) was measured to be ~35 e− for unity gain. With internal gain set to 35 or above, the effective read noise contribution was measured to be <1 e. To enhance the sensitivity for detecting ~30 keV $^{125}$I γ-rays, a camera gain of 200 was used. The effective read noise at this gain setting was still <1 e−.

Effective dynamic range of the system can be estimated. In one example, the effective dynamic range of the system for the gain of 200 was estimated as follows. The full-well capacity of the e2V 887 EMCCD image pixels is 250K e$^-$ and that of the gain register pixel is 850 K e$^-$. Thus, when the CCD is operated at the gain of 200, the maximum usable pixel well capacity is 850,000/200 or 4,250 electrons, or 12 bits. Since the dark and read noise is negligible, most of this dynamic range is useful and is quite adequate for detecting individual γ-photons.

To measure sensitivity, the EMCCD camera was mounted on an optical bench and a laser beam was used to illuminate pixels through the fiber optic window. A 540 nm collimated laser beam was made incident on the EMCCD. The camera was operated at 10 fps, and at a gain of ~50. The photon flux was measured with a calibrated photodiode (e.g., Hamamatsu model 1336-8BQ). Metallic neutral density filters (e.g., commercially available from ThorLabs, Inc.) were added in the path of the laser beam to attenuate the incident flux until the image could be barely seen on the monitor. The measured fluence for this setting was ~1 photon/pixel, indicating that the camera was sensitive to ~1 green photons. It should be noted that conventional front illuminated CCDs cannot register a signal below ~30 optical photon. This significant result illustrates that an exemplary prototype detector based on back illuminated EMCCD is able to detect extremely low levels of light generated by gamma-ray interactions in the scintillator screens.

Detector Integration and Evaluation

The detectors of the invention, including those optically coupled with a high sensitivity and high speed EMCCD, can be used in photon counting mode during radionuclide imaging. In one example, pixellated CsI(Tl) scintillators coupled to the fiber optic window of the EMCCD were evaluated in photon counting mode. The detectors of the present invention additionally allow identification of pixel clusters corresponding to single photon events (e.g., single gamma-ray events) and use of this information to localize the events with high precision. The energy and position information obtained by these measurements can then be used to improve the spatial resolution of a radiation detector of the present invention, including a gamma-ray camera or detector.

Response Uniformity Measurements

Figure 10:
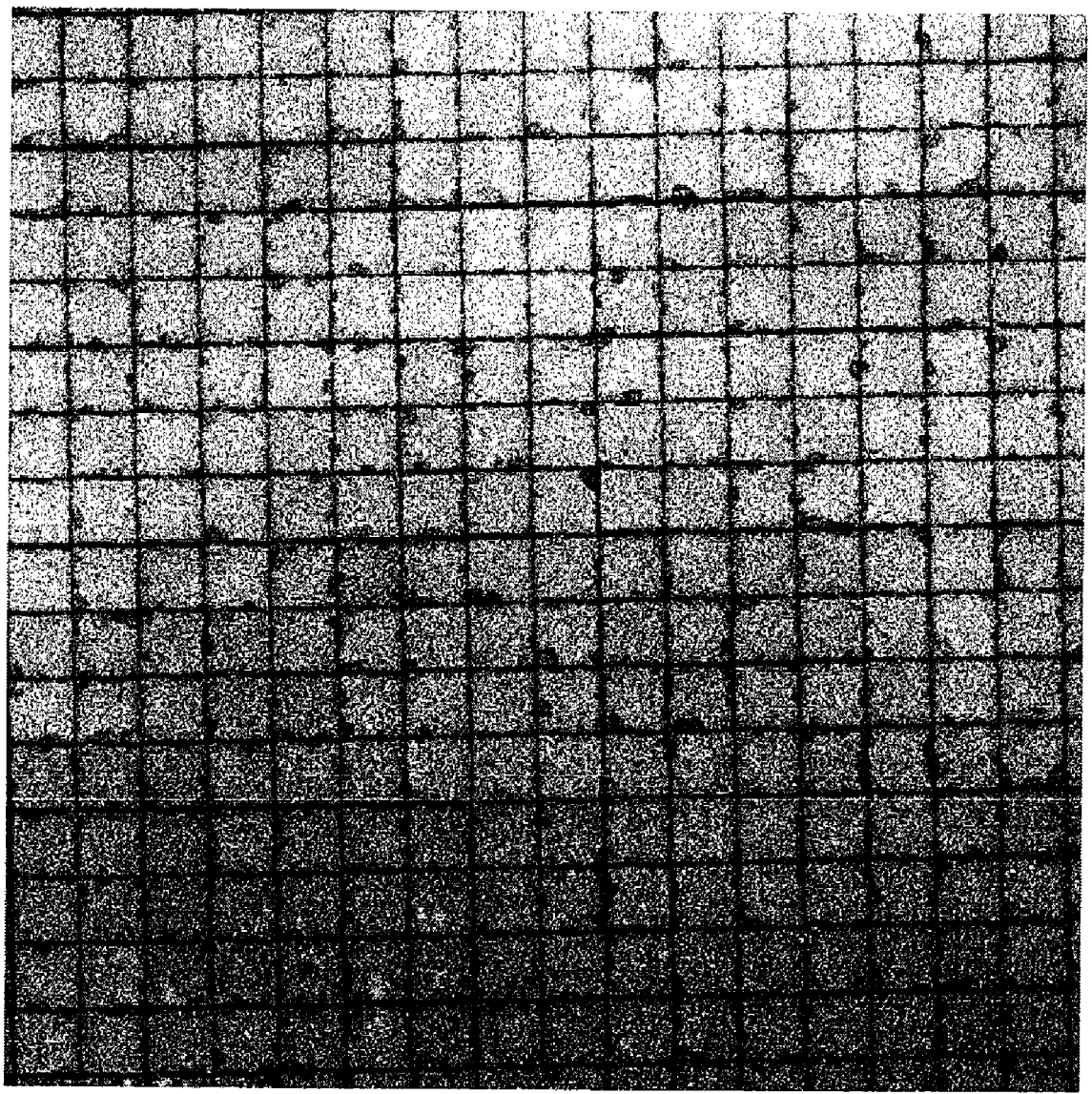
FIG. 10 shows a flood image obtained with a 3 mm thick pixellated CsI(Tl) scintillator crystal according to one embodiment of the present invention.

The pixellated scintillators typically include a high degree of uniformity over the area of the scintillator. In one embodiment, a flood image of a pixellated crystal was obtained by exposing the detector to gamma radiation from a 140 keV $^{99m}$Tc point source (small amount of $^{99m}$Tc introduced into a capillary). No collimator was used for this part of the tests. A 3 mm thick CsI(Tl) crystal with 250 μm pixels was coupled to the EMCCD for these tests. FIG. 10 displays an image obtained in 10 seconds. The 250 μm pixels can be clearly seen in this image, illustrating the excellent intrinsic resolution of the EMCCD. The measured response non-uniformity over the area of the scintillator was found to be <5%. Such data can further be used for flood field corrections including, for example, corrections to the acquired SPECT projections as is described below.

Single Gamma-Photon Imaging

Figure 11:
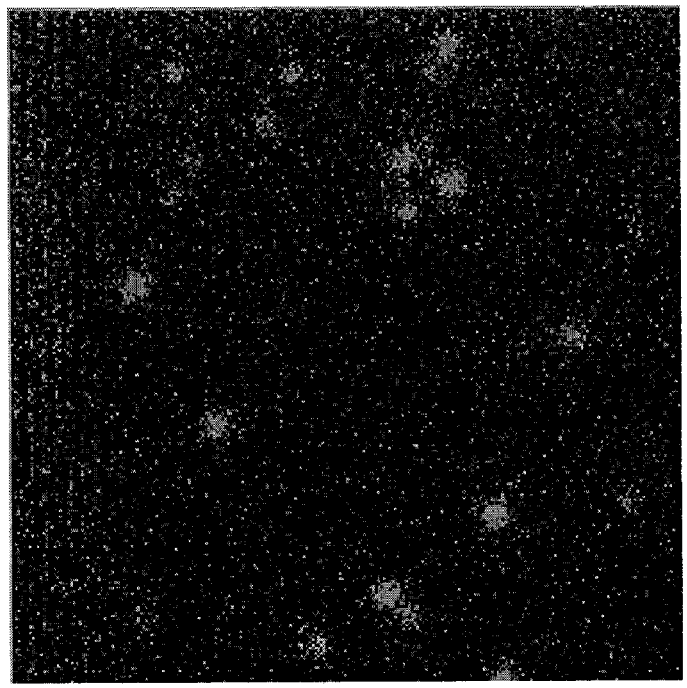
FIG. 11A and FIG. 11B show single photon "hits" from an un-collimated $^{57}$Co source acquired with a 500 μm thick pixellated CsI(Tl) crystal and an EMCCD readout (FIG. 11A); and one frame of a slit image obtained using a $^{99m}$Tc source (FIG. 11B).
Figure 11:
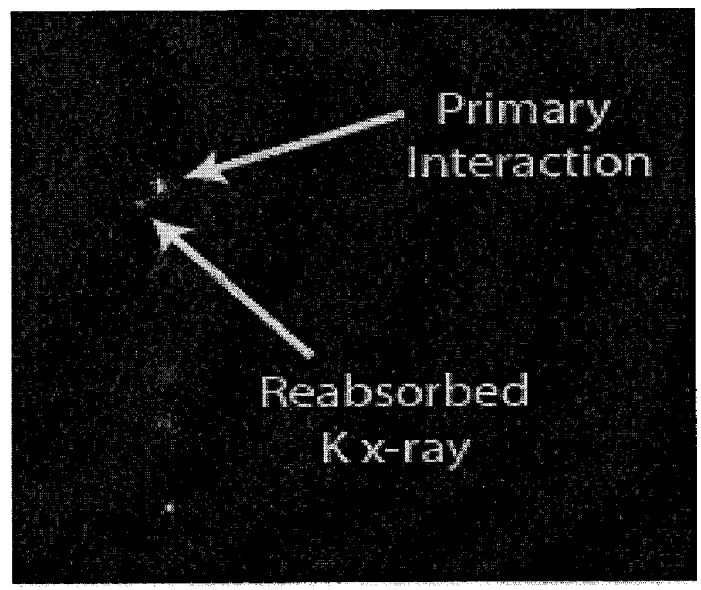

As set forth above, the detectors of the present invention are suitable for single photon counting. In one embodiment, for example, intrinsic resolution was measured using a 500 μm thick pixellated CsI(Tl) scintillator pressure coupled to the 1:1 fiber optic window of the EMCCD. Initially, the detector operated in full resolution mode and was exposed to a flood source of 122 keV $^{57}$Co gamma-rays. Optical photons generated by the γ-ray interactions in the scintillator were sampled over multiple CCD pixels and were recorded with the camera operating in photon-counting mode (10 fps). As shown in FIG. 11A, individual γ-ray interaction response differ from one another in light output and spatial variance due to the depth of interaction. FIG. 11B shows another data frame where K x-rays are clearly resolved apart from the primary interactions, demonstrating the excellent sensitivity and spatial resolution of the detector.

Spatial Resolution Measurements

Figure 12:
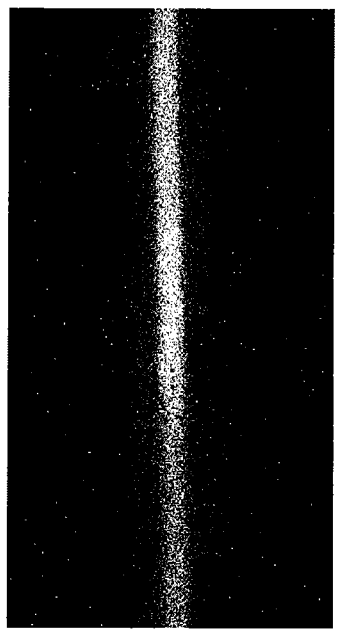
FIG. 12A through FIG. 12D show a 50 second image of a 50 μm wide slit obtained using a 99mTc source (FIG. 12A); a line profile showing about 400 μm FWHM resolution in integrating mode (FIG. 12B); a slit image with a EMCCD operated in photon counting mode (FIG. 12C); and a line profile corresponding to FIG. 12C (FIG. 12D) showing improved (250 μm) FWHM resolution.
Figure 12:
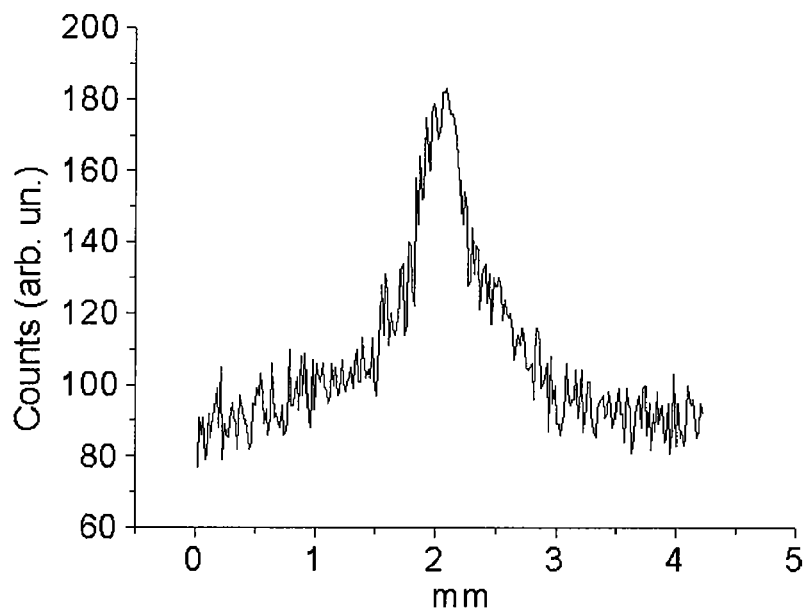
Figure 12:
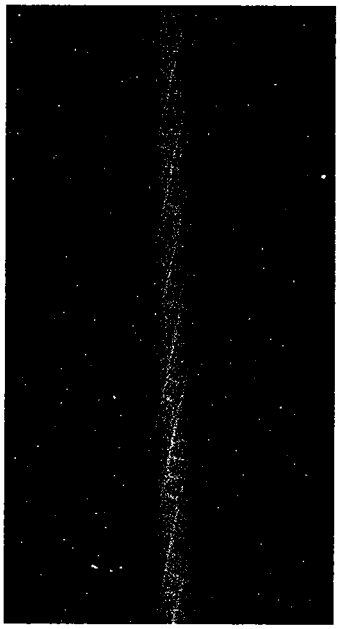
Figure 12:
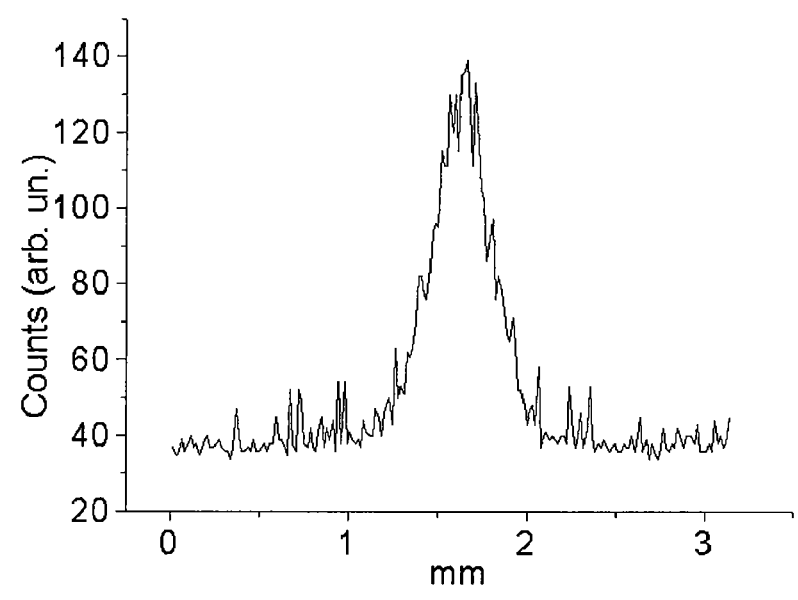

To test the resolution of an exemplary pixellated detector, a 3 mm thick CsI(Tl) crystal with 250 μm pixel pitch was coupled to the EMCCD via its 1:1 fiber optic window. A 50 μm lead slit was placed on the detector and the detector was illuminated with a 140 keV, $^{99m}$Tc γ-ray source placed at a distance of 1 meter. Initially the detector was operated in an integration mode where the slit image was acquired for a period of 50 seconds. The resulting image is shown in FIG. 12A and the corresponding line profile is shown in FIG. 12B. The measured FWHM resolution in this configuration was found to be ~400 μm.

Operating the EMCCD in photon counting mode enables estimation of the photon-scintillator interaction position better than by analyzing the spread of the light distribution. In one example, photon counting mode the EMCCD was operated at the rate of 30 fps and a set of 10,000 frames was acquired. To estimate the interaction position, a background image was first subtracted from each data frame and the image was then thresholded slightly above the noise. Each frame was searched for contiguous regions of signal above the threshold, which were then identified as individual events. A centroid estimation was calculated on a window (e.g., 16×16 pixels) around the identified event to better estimate the interaction position. After centroid estimations were calculated, an image was generated containing the centroid position of each of the extracted gamma-ray interactions. As can be seen from FIGS. 12C and 12D, this resulted in improving the spatial resolution to ~250 μm FWHM, which is a significant improvement compared to the resolution in an integration mode. Note that the centroid approach allows for achieving the intrinsic resolution of the pixellated scintillator. It should also be noted that no scatter correction has been applied to the above data. By correcting for scatter, even better resolution may be obtained.

Previous analysis has demonstrated that the EMCCD based detector can provide intrinsic resolution of 45 μm FWHM (not shown). It is noteworthy that these measurements were made using a 450 μm thick columnar CsI(Tl), spatial resolution generally decreases with increasing scintillator thickness. Thus, the measured resolution of 250 μm using a 3 mm thick pixellated CsI(Tl) scintillator is a remarkable accomplishment in terms of both, spatial resolution and detector efficiency.

As set forth above, detectors including beam-oriented pixellated scintillators of the present invention can be used in various radiation imaging applications. One imaging application includes SPECT, including small animal SPECT, though the application of beam-oriented scintillators is not limited to this application. Other applications can include, for example, radioisotope monitoring and configuration definition, including remote monitoring, x-ray imaging and the like. In x-ray imaging, for instance, a typical digital radiography setup for skeletal imaging will have a source to detector distance of about 1 m, and a up to 14×17-inch plate. For the case of the x-ray tube centered over the center of the plate, the largest illumination angle is about 12 degrees, leading to 0.6 mm spread for a 3 mm thickness detector. In commercial whole body imaging, plates can be stacked to cover the spine and leg bones so that the imaged length is on the order of 150 cm and the illumination angles exceed 35 degrees. In one embodiment, very thin scintillators can be utilized to maximize spatial resolution. Thicker, more efficient beam-oriented scintillators may be used where significant radiation dose reductions are desired, and may include, for example, applications involving radiation sensitive patients or children. Selection of thicker, more efficient beam-oriented scintillators and lower radiation doses be desired in many other situations, including, for example, where an imaging assembly and imaged object undergo relative rotation so that images can be obtained from a multiplicity of angles so as to generate 3-D reconstructions of the object, e.g., by known means for cone beam geometry reconstruction.

It is understood that the examples and embodiments described herein are for illustrative purposes only and that various modifications or changes in light thereof will be suggested to persons skilled in the art and are to be included within the spirit and purview of this application and scope of the appended claims. Numerous different combinations are possible, and such combinations are considered to be part of the present invention.

What is claimed is:

1. A radiation detection device, comprising:
a two-dimensional, beam-oriented monolithic pixellated scintillator, the scintillator having a first pixel having a first pixel axis and a second pixel having a second pixel axis, wherein the first and second axes are at an angle relative to each other, and wherein each axis is substantially parallel to a predetermined beam direction for illuminating the corresponding pixel.

2. The device of claim 1, wherein the scintillator comprises a two-dimensional array of pixels.

3. The device of claim 1, wherein pixels of the scintillator comprise a rectangular, rhomboidal, triangular, or hexagonal shape.

4. The device of claim 1, wherein the pixels are formed by laser micromachining.

5. The device of claim 1, wherein the scintillator comprises inter-pixel grooves.

6. The device of claim 5, wherein the inter-pixel grooves comprise V-shaped grooves.

7. The device of claim 5, wherein the inter-pixel grooves comprise substantially parallel-sided grooves.

8. The device of claim 5, further comprising a heavy element slurry deposited in inter-pixel grooves of the scintillator.

9. The device of claim 5, wherein the pixels comprise a two-dimensional monolithic array.

10. The device of claim 9, wherein the grooves extend no farther through the slab than 200 μm from the uncut surface of the slab.

11. The device of claim 1, wherein the scintillator material comprises CsI(Tl).

12. The device of claim 1, wherein the scintillator material comprises Cerium-doped LaBr3.

13. The device of claim 1, wherein the scintillator is a crystal or a film.

14. The device of claim 1, wherein spacing between pixels comprises about 100 µm to about 1 mm.

15. The device of claim 1, wherein the thickness of the scintillator is about 250 µm to about 1.5 cm.

16. The device of claim 1, wherein the thickness of the target detection efficiency of the scintillator is about 60% to about 90%.

17. The device of claim 1, further comprising a reflective layer coating at least a portion of a pixel.

18. The device of claim 1, further comprising a protective layer coating at least a portion of a pixel.

19. The device of claim 1, wherein the scintillator is disposed on a substantially planar surface of a substrate.

20. The device of claim 19, wherein the substrate comprises a carbon, beryllium, boron, carbide, or aluminum substrate.

21. The device of claim 19, wherein a side of the substrate opposite the scintillator faces a direction from which a radiation beam is directed.

22. The device of claim 19, wherein a side of the substrate opposite the scintillator faces a photodetector and the pixels face a direction from which the radiation beam is directed.

23. The device of claim 1, wherein the scintillator comprises a crystal scintillator glued to a substrate.

24. The device of claim 1, further comprising a photodetector optically coupled to the scintillator.

25. A radiation detection device, comprising:
a two-dimensional beam-oriented monolithic pixellated scintillator having an array of pixels, each pixel of the array having a pixel axis oriented to substantially match a predetermined illumination direction of a radiation beam reaching the pixel, at least one of the pixels having an axis that is at an angle relative to another pixel axis of the array.

26. The device of claim 25, further comprising a photodetector optically coupled to the scintillator.

27. The device of claim 26, wherein the photodetector is an EMCCD.

28. The device of claim 25, wherein the scintillator comprises CsI(Tl).

29. The device of claim 25, wherein the pixels comprise a two-dimensional monolithic array.

30. The device of claim 25, further comprising a collimator.

31. The device of claim 30, wherein the collimator comprises a single pinhole, multipinhole, a coded aperture, a convergent multihole collimator, or a divergent multihole collimator.

32. The device of claim 25, the array comprising a region of pixels with each pixel of the region oriented such that the axes of the pixels of the region converge on substantially the same point.

33. A radiation detection device for detecting radiation beams produced by a radiation source and illuminating the detection device at a plurality of different locations, the device comprising a two-dimensional pixellated monolithic scintillator having a plurality of pixels, wherein each pixel comprises a pixel axis that is oriented substantially along a predetermined illumination direction of a radiation beam reaching the corresponding pixel, and wherein at least one of the pixels has a pixel axis that is oriented at an angle relative to a pixel axis of another pixel of the plurality; and further comprising a collimator spaced from the scintillator and disposed between the radiation source and the scintillator.

34. The device of claim 33, wherein the radiation source is a radioactive source.

35. The device of claim 33, wherein the radiation sources is an electromechanical device.

36. The device of claim 33, wherein the radiation source is a radiopharmaceutical agent.

37. An X-ray imaging device, comprising:
a two-dimensional monolithic imaging plate comprising a beam-oriented pixellated scintillator having an array of pixels, each pixel of the array having a pixel axis oriented to substantially match a predetermined illumination direction of a radiation beam reaching the pixel, at least one of the pixels having an axis that is at an angle relative to another pixel axis of the array; and
an X-ray source spaced from the imaging plate.

38. The device of claim 37, wherein the X-ray source and imaging plate are spaced such that a focal point of pixels of the array and a focal point of the X-ray source are substantially coincident.

39. The device of claim 37, further comprising a means for rotating an object for imaging that is placed between the imaging plate and the X-ray source.

40. The device of claim 39, wherein the X-ray source and the imaging plate are rotatable about an imaged object while maintaining substantial coincidence between the focal point of the pixels and the focal point of the X-ray source.

41. The device of claim 37, further comprising a plurality of imaging plates, each imaging plate comprising a beam-oriented pixellated scintillator.

42. A method of fabricating a beam-oriented pixellated scintillator, comprising:
forming a plurality of grooves in a slab of scintillator material to form an array of pixels, each pixel of the array having a pixel axis oriented to substantially match a predetermined illumination direction of a radiation beam reaching the pixel, at least one of the pixels having an axis that is at an angle relative to another pixel axis of the array.

43. The method of claim 42, wherein forming comprises laser micromachining.

44. The method of claim 43, wherein laser micromachining a groove comprises a single pass of a laser beam across the slab of scintillator material.

45. The method of claim 44, further comprising blowing a dry gas in a groove while forming that groove by single pass laser micromachining.

46. The method of claim 43, wherein an additional laser beam is used to score an initial cut on a surface of the slab.

47. The method of claim 43, wherein an additional laser beam is used to heal at least one surface of the grooves.

48. The method of claim 42, wherein the grooves comprise V-shaped grooves.

49. The method of claim 42, wherein the grooves comprise substantially parallel-sided grooves.

50. The method of claim 42, wherein the grooves extend partially through the slab of scintillator material.

51. The method of claim 42, wherein the grooves extend no farther through the slab than 200 µm from the uncut surface of the slab.

52. The method of claim 42, wherein the scintillator material comprises CsI(Tl).

53. The method of claim 42, wherein the scintillator material comprises Cerium-doped LaBr3.

54. The method of claim 42, further comprising re-diffusing a dopant into one or more grooves of the scintillator.

55. The method of claim 42, further comprising depositing a reflective layer on at least a portion of a pixel.

56. The method of claim 55, wherein the depositing of the reflective layer comprises pouring paint on the machined scintillator slab, placing the slab in an evacuated chamber, and spinning the slab to remove excess paint.

57. The method of claim 42, further comprising surface polishing the slab to open pixels for light coupling to a photodetector.

58. The method of claim 42, further comprising depositing a protective layer on at least a portion of a pixel.

59. The method of claim 42, where the scintillator is disposed on a substrate.

60. The method of claim 42, further comprising providing a fixed laser beam, and mounting the slab of scintillator material on a goniometer, the goniometer mounted on an x,y table.

61. The method of claim 42, wherein the center to center distance between pixels of the array is between 100 μm and 1 mm.

62. The method of claim 42, wherein the thickness of the scintillator is between 250 μm and 1.5 cm.

63. A method of performing radiation detection, comprising:

providing a radiation detector comprising a two-dimensional beam-oriented pixellated monolithic scintillator having an array of pixels, each pixel of the array having a pixel axis oriented to substantially match a predetermined illumination direction of a radiation beam reaching the pixel, at least one of the pixels having an axis that is at an angle relative to another pixel axis of the array; and positioning a target within a field of view of the radiation detector as to detect emissions or absorption from the target.

* * * * *